US011235008B2

(12) United States Patent
Farmer et al.

(10) Patent No.: US 11,235,008 B2
(45) Date of Patent: Feb. 1, 2022

(54) PROBIOTIC SPORTS NUTRITION COMPOSITIONS

(75) Inventors: Sean Farmer, Miami, FL (US); David Keller, University Heights, OH (US); Andrew R. Lefkowitz, Mayfield Heights, OH (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 0 days.

(21) Appl. No.: 13/434,401

(22) Filed: Mar. 29, 2012

(65) Prior Publication Data

US 2012/0251512 A1 Oct. 4, 2012

Related U.S. Application Data

(60) Provisional application No. 61/469,924, filed on Mar. 31, 2011.

(51) Int. Cl.
| | |
|---|---|
| *A61K 35/742* | (2015.01) |
| *A23L 33/135* | (2016.01) |
| *A23L 33/17* | (2016.01) |
| *A23L 33/19* | (2016.01) |
| *A23K 20/147* | (2016.01) |
| *A23K 20/158* | (2016.01) |
| *A23K 20/174* | (2016.01) |
| *A23K 20/20* | (2016.01) |
| *A23K 50/20* | (2016.01) |
| *A23K 50/40* | (2016.01) |
| *A23K 20/10* | (2016.01) |
| *A61K 31/202* | (2006.01) |
| *A61K 38/01* | (2006.01) |

(52) U.S. Cl.
CPC ............ *A61K 35/742* (2013.01); *A23K 20/10* (2016.05); *A23K 20/147* (2016.05); *A23K 20/158* (2016.05); *A23K 20/174* (2016.05); *A23K 20/20* (2016.05); *A23K 50/20* (2016.05); *A23K 50/40* (2016.05); *A23L 33/135* (2016.08); *A23L 33/17* (2016.08); *A23L 33/19* (2016.08); *A61K 31/202* (2013.01); *A61K 38/018* (2013.01)

(58) Field of Classification Search
None
See application file for complete search history.

(56) References Cited

U.S. PATENT DOCUMENTS

| | | | |
|---|---|---|---|
| 3,091,572 A | 5/1963 | Luedemann et al. | |
| 3,840,684 A | 10/1974 | Fazzina et al. | |
| 4,110,477 A | 8/1978 | Naruse et al. | |
| 4,144,346 A | 3/1979 | Heeres et al. | |
| 4,321,258 A | 3/1982 | Dunlap | |
| 4,323,651 A | 4/1982 | Long et al. | |
| 4,695,546 A | 9/1987 | Aiba et al. | |
| 4,756,913 A | 7/1988 | Khorkova et al. | |
| 4,956,177 A | 9/1990 | King et al. | |
| 4,980,180 A | 12/1990 | Cully et al. | |
| 5,021,344 A | 6/1991 | Armau et al. | |
| 5,079,164 A | 1/1992 | Kirkovits et al. | |
| 5,102,800 A | 4/1992 | Hirikoshi | |
| 5,176,911 A | 1/1993 | Tosi et al. | |
| 5,200,336 A | 4/1993 | Kong et al. | |
| 5,266,315 A | 11/1993 | Taguchi et al. | |
| 5,334,516 A | 8/1994 | Muramatsu et al. | |
| 5,413,960 A | 5/1995 | Dobrogosz et al. | |
| 5,427,777 A | 6/1995 | St. Pierre et al. | |
| 5,439,678 A | 8/1995 | Dobrogosz et al. | |
| 5,439,995 A | 8/1995 | Bailly et al. | |
| 5,531,988 A | 7/1996 | Paul | |
| 5,531,989 A | 7/1996 | Paul | |
| 5,534,253 A | 7/1996 | Casas et al. | |
| 5,607,669 A | 3/1997 | Mandeville, III et al. | |
| 5,665,354 A | 9/1997 | Neyra et al. | |
| 5,785,990 A | 7/1998 | Langrehr | |
| 5,895,672 A | 4/1999 | Cooper | |
| 5,968,569 A | 10/1999 | Cavadini et al. | |
| 6,080,401 A | 6/2000 | Reddy et al. | |
| 6,132,710 A | 10/2000 | Panigrahi et al. | |
| 6,461,607 B1 | 10/2002 | Farmer | |
| 6,531,126 B2 | 3/2003 | Farmer | |
| 6,537,543 B1 | 3/2003 | Minakawa | |
| 6,645,506 B1 | 11/2003 | Farmer | |
| 6,716,435 B1 | 4/2004 | Farmer et al. | |
| 6,723,326 B1 | 4/2004 | Farmer | |
| 6,733,751 B2 | 5/2004 | Farmer | |
| 6,811,786 B1 | 11/2004 | Farmer et al. | |
| 6,849,256 B1 * | 2/2005 | Farmer ................. | A61K 35/742 424/93.46 |
| 6,849,265 B2 * | 2/2005 | Butts ...................... | A61K 8/89 424/400 |

(Continued)

FOREIGN PATENT DOCUMENTS

| | | |
|---|---|---|
| CN | 1507812 A | 6/2004 |
| DE | 4132296 C1 | 12/1992 |

(Continued)

OTHER PUBLICATIONS

Max Muscle, PR Newswire, http://search.proquest.com/professional/docview/679196304? accountid=142257, Feb. 10, 2009 (last visited Feb. 21, 2013).*
http://www.oregondairycouncil.org/what_is_normal/pdf/whey_and_sports.pdf, last visited on Jan. 10, 14. Available Feb. 2002.*
ATCC Accession No. 31284, retrieved Apr. 2, 2012.
Worthley et al. "A Human, Double-Blind, Placebo-Controlled, Crossover Trial of Prebiotic, Probiotic, and Synbiotic Supplementation: Effects on Luminal, Inflammatory, Epigenetic, and Epithelial Biomarkers of Colorectal Cancer." *Am. J. Clin. Nutr.* 90.3(2009):578-586.
Keller et al. "*Bacillus coagulans* as a Probiotic." *Food Sci. Tech. Bullet.* 7.7(2010):103-109.

(Continued)

*Primary Examiner* — Vera Afremova
(74) *Attorney, Agent, or Firm* — Sughrue Mion, PLLC

(57) ABSTRACT

The present application relates to nutritional compositions comprising lactic acid-producing bacteria.

35 Claims, No Drawings

(56) References Cited

U.S. PATENT DOCUMENTS

| | | |
|---|---|---|
| 6,905,692 B2 | 6/2005 | Farmer |
| 7,024,497 B1 | 4/2006 | Maffezoni |
| 7,025,974 B2 | 4/2006 | Farmer et al. |
| 7,048,950 B2 | 5/2006 | Farmer |
| 7,232,571 B2 | 6/2007 | Farmer et al. |
| 7,371,407 B2 | 5/2008 | Farmer |
| 7,374,753 B1 | 5/2008 | Farmer et al. |
| 7,507,402 B1 | 3/2009 | Farmer et al. |
| 7,541,042 B2 | 6/2009 | Farmer |
| 7,544,363 B2 | 6/2009 | Farmer |
| 7,555,715 B2 | 6/2009 | Randall et al. |
| 7,700,093 B2 | 4/2010 | Farmer et al. |
| 7,708,988 B2 | 5/2010 | Farmer |
| 7,713,726 B2 | 5/2010 | Farmer |
| 7,767,203 B2 | 8/2010 | Farmer et al. |
| 7,807,151 B2 | 10/2010 | Farmer |
| 7,807,185 B2 | 10/2010 | Farmer |
| 7,854,927 B2 | 12/2010 | Farmer et al. |
| 7,982,066 B2 * | 7/2011 | Scheele ............... A61P 43/00 562/553 |
| 8,097,247 B2 | 1/2012 | Farmer |
| 8,187,590 B2 | 5/2012 | Farmer |
| 8,273,346 B2 | 9/2012 | Farmer et al. |
| 8,277,799 B2 | 10/2012 | Farmer |
| 8,343,484 B2 | 1/2013 | Farmer et al. |
| 8,349,337 B1 | 1/2013 | Farmer et al. |
| 8,409,591 B2 | 4/2013 | Farmer et al. |
| 8,568,743 B2 | 10/2013 | Farmer et al. |
| 8,568,744 B2 | 10/2013 | Farmer et al. |
| 8,697,055 B2 | 4/2014 | Farmer |
| 8,821,854 B2 | 9/2014 | Farmer et al. |
| 9,192,659 B2 | 11/2015 | Farmer et al. |
| 9,220,736 B2 | 12/2015 | Farmer et al. |
| 9,288,998 B2 * | 3/2016 | Marsland ............... A23L 7/13 |
| 9,301,982 B2 | 4/2016 | Lefkowitz |
| 9,446,111 B2 | 9/2016 | Farmer et al. |
| 9,597,286 B2 | 3/2017 | Lefkowitz |
| 9,622,502 B2 | 4/2017 | Farmer et al. |
| 9,757,442 B2 | 9/2017 | Farmer et al. |
| 2001/0006644 A1 | 7/2001 | Bova et al. |
| 2003/0031659 A1 | 2/2003 | Farmer |
| 2003/0138936 A1 | 7/2003 | Mizuguchi et al. |
| 2003/0185811 A1 | 10/2003 | Teasdale et al. |
| 2004/0010510 A1 | 1/2004 | Hotti |
| 2004/0071685 A1 | 4/2004 | Houston et al. |
| 2004/0161422 A1 | 8/2004 | Ranganathan |
| 2004/0161522 A1 | 8/2004 | Toves |
| 2004/0175459 A1 | 9/2004 | Ting |
| 2005/0129823 A1 * | 6/2005 | Dohl et al. .................. 426/549 |
| 2005/0154682 A1 | 7/2005 | Taylor |
| 2005/0202145 A1 | 9/2005 | Dorr et al. |
| 2005/0232909 A1 | 10/2005 | Farmer |
| 2006/0112584 A1 | 6/2006 | Jones |
| 2006/0184538 A1 | 8/2006 | Randall et al. |
| 2007/0059400 A1 | 3/2007 | Goto et al. |
| 2008/0166449 A1 | 7/2008 | Kabse et al. |
| 2008/0206212 A1 | 8/2008 | McMahon et al. |
| 2008/0274153 A1 | 11/2008 | Farmer |
| 2008/0305096 A1 | 12/2008 | Verdegem et al. |
| 2009/0186057 A1 | 7/2009 | Farmer et al. |
| 2009/0186126 A1 | 7/2009 | Farmer et al. |
| 2009/0232941 A1 | 9/2009 | Farmer |
| 2010/0210000 A1 | 8/2010 | Farmer et al. |
| 2011/0195154 A1 | 8/2011 | Farmer |
| 2011/0217275 A1 | 9/2011 | Opheim |
| 2011/0274676 A1 | 11/2011 | Farmer et al. |
| 2012/0128832 A1 * | 5/2012 | Smiht ............... A21L 2/66 426/106 |
| 2012/0251512 A1 | 10/2012 | Farmer et al. |
| 2013/0164398 A1 | 6/2013 | Farmer |
| 2013/0195824 A1 | 8/2013 | Farmer et al. |
| 2013/0216577 A1 | 8/2013 | Farmer et al. |
| 2013/0251695 A1 | 9/2013 | Farmer et al. |
| 2013/0344046 A1 | 12/2013 | Farmer et al. |
| 2014/0242051 A1 | 8/2014 | Farmer |
| 2015/0044317 A1 | 2/2015 | Farmer et al. |
| 2015/0313951 A1 | 11/2015 | Cash et al. |
| 2016/0213612 A1 | 7/2016 | Lefkowitz |
| 2016/0213613 A1 | 7/2016 | Lefkowitz |
| 2016/0213614 A1 | 7/2016 | Lefkowitz |
| 2016/0213615 A1 | 7/2016 | Lefkowitz |
| 2017/0000872 A1 | 1/2017 | Farmer et al. |
| 2017/0035813 A1 | 2/2017 | Farmer et al. |
| 2017/0189331 A1 | 7/2017 | Lefkowitz |
| 2017/0189457 A1 | 7/2017 | Farmer et al. |

FOREIGN PATENT DOCUMENTS

| | | |
|---|---|---|
| EP | 0307158 A2 | 3/1989 |
| EP | 0457539 A1 | 11/1991 |
| EP | 0862863 A2 | 9/1998 |
| EP | 1020123 A1 | 7/2000 |
| EP | 1112693 A1 * | 7/2001 |
| EP | 1344458 A1 | 9/2003 |
| EP | 1810579 A1 | 7/2007 |
| GB | 1040278 A | 8/1966 |
| JP | 56002908 | 1/1981 |
| JP | 62061572 A | 3/1987 |
| JP | 6463389 A | 3/1989 |
| JP | 6483025 A | 3/1989 |
| JP | 04041434 | 2/1992 |
| JP | 4082827 A | 3/1992 |
| JP | 4158771 A | 6/1992 |
| JP | 6166626 A | 6/1994 |
| JP | 06343419 A | 12/1994 |
| JP | 7298833 A | 11/1995 |
| JP | 08175921 | 7/1996 |
| JP | 9194384 A | 7/1997 |
| JP | 3052131 U | 9/1998 |
| JP | 10306028 A | 11/1998 |
| JP | 11169145 A | 6/1999 |
| JP | 11335285 A | 12/1999 |
| JP | 2000093162 A | 4/2000 |
| JP | 2000102378 A | 4/2000 |
| JP | 2001252012 A | 9/2001 |
| JP | 2002114671 A | 4/2002 |
| JP | 2003513649 A | 4/2003 |
| JP | 2004337125 A | 12/2004 |
| JP | 2005137357 A | 6/2005 |
| JP | 2006025621 A | 2/2006 |
| JP | 2006254837 A | 9/2006 |
| JP | 2007000140 A | 1/2007 |
| JP | 2007044014 A | 2/2007 |
| JP | 2008013543 A | 1/2008 |
| JP | 4158774 | 10/2008 |
| TW | I228974 B | 3/2005 |
| WO | WO-8905849 A1 | 6/1989 |
| WO | WO-9314187 A1 | 7/1993 |
| WO | WO-9411492 A1 | 5/1994 |
| WO | WO-9611014 A1 | 4/1996 |
| WO | WO-9702757 A1 | 1/1997 |
| WO | WO-9729762 A1 | 8/1997 |
| WO | WO-9734615 A1 | 9/1997 |
| WO | WO-9847374 A1 | 10/1998 |
| WO | WO-9854982 A1 | 12/1998 |
| WO | WO-99032451 A1 | 7/1999 |
| WO | WO 99/49877 * | 10/1999 |
| WO | WO-9949877 A2 | 10/1999 |
| WO | WO-0007606 A2 | 2/2000 |
| WO | WO-0010582 A2 | 3/2000 |
| WO | WO-0061201 A1 | 10/2000 |
| WO | WO-01 13956 A2 | 3/2001 |
| WO | WO-0113927 A2 | 3/2001 |
| WO | WO-0134168 A1 | 5/2001 |
| WO | WO-0208285 A2 | 1/2002 |
| WO | WO-03039260 A2 | 5/2003 |
| WO | WO-2004004747 A1 | 1/2004 |
| WO | WO-2004008870 A1 | 1/2004 |
| WO | WO-2005019417 A2 | 3/2005 |
| WO | WO-2005055934 A2 | 6/2005 |
| WO | WO-05092122 A1 | 10/2005 |
| WO | WO-2005092122 A1 | 10/2005 |
| WO | WO-2005117926 A1 | 12/2005 |
| WO | WO-2006/090729 A1 | 8/2006 |

(56) References Cited

FOREIGN PATENT DOCUMENTS

| WO | WO-2007/058027 A1 | 5/2007 |
|----|----|----|
| WO | WO-2008/112296 A1 | 9/2008 |
| WO | WO-2009102575 A1 | 8/2009 |
| WO | WO-10045541 A1 | 4/2010 |

OTHER PUBLICATIONS

Allos, B.M., "Association between Campylobacter Infection and Guillain-Barre Syndrome", J. Infect. Dis. 176: S125-S128 (1997).
Ara et al. "Effect of Spore-Bearing Lactic Acid-Forming Bacteria (Bacillus coagulans SANK 70258) Administration on the Intestinal Environment, Defecation Frequency, Fecal Characteristics and Dermal Characteristics in Humans and Rats." MicrobialEcol. Health Dis. 14.1(2002):4-13.
Araki et al. "Occurrence of N-Nonsubstituted Glucosamine Residues in Peptidoglycan of Lysozyme-Resistant Cell Walls from *Bacillus cereus.*" *J. Biol. Chem.* 247.19(1972):6312-6322.
Arthur et al. "Genetics and Mechanisms of Glycopeptide Resistance in Enterococci." *Antimicrob. Agents Chemother.* 37.8(1993):1563-1571.
ATCC Catalogue of Bacteria and Bacteriophages Accession No. 11014, Retrieved Aug. 11, 2009.
ATCC Catalogue of Bacteria and Bacteriophages Accession No. 11369, Retrieved Aug. 11, 2009.
ATCC Catalogue of Bacteria and Bacteriophages Accession No. 15949, Retrieved Aug. 11, 2009.
*ATCC Catalogue of Bacteria and Bacteriophages*, Accession No. 10545, Retrieved Jan. 26, 2010.
*ATCC Catalogue of Bacteria and Bacteriophages*, Accession No. 12245, Retrieved Jan. 26, 2010.
*ATCC Catalogue of Bacteria and Bacteriophages*, Accession No. 23492, Retrieved Jan. 26, 2010.
*ATCC Catalogue of Bacteria and Bacteriophages*, Accession No. 23493, Retrieved Jan. 26, 2010.
*ATCC Catalogue of Bacteria and Bacteriophages*, Accession No. 23494, Retrieved Jan. 26, 2010.
*ATCC Catalogue of Bacteria and Bacteriophages*, Accession No. 23495, Retrieved Jan. 26, 2010.
*ATCC Catalogue of Bacteria and Bacteriophages*, Accession No. 23498, Retrieved Jan. 26, 2010.
*ATCC Catalogue of Bacteria and Bacteriophages*, Accession No. 23549, Retrieved Jan. 26, 2010.
*ATCC Catalogue of Bacteria and Bacteriophages*, Accession No. 35670, Retrieved Jan. 26, 2010.
*ATCC Catalogue of Bacteria and Bacteriophages*, Accession No. 51232, Retrieved Jan. 26, 2010.
*ATCC Catalogue of Bacteria and Bacteriophages*, Accession No. 7050, Retrieved Jan. 26, 2010.
*ATCC Catalogue of Bacteria and Bacteriophages*, Accession No. 8038, Retrieved Jan. 26, 2010.
Baker et al. "Growth Requirements of 94 Strains of Thermophilic bacilli." *CA. J. Microbiol.* 6(1960):557-563.
Banerjee et al. "Bacillus Infections in Patients With Cancer." *Arch. Intern. Med.* 148.8(1988):1769-1774.( Abstract Only).
Barefoot et al. "Antibiosis Revisited: Bacteriocins Produced by Dairy Starter Cultures 1." *J. Dairy Sci.* 76.8(1993):2366-2379.
Baron. "Original Research: A Patented Strain of *Bacillus coagulans* Increased Immune Response to Viral Challenge." *Postgrad. Med.* 121.2(2009):114-118.
Bernet et al. "Adhesion of Human Bifidobacterial Strains to Cultured Human Intestinal Epithelial Cells and Inhibition of Enteropathogen-Cell Interactions." *Appl. Environ. Microbiol.* 59.12(1993): 4121-4128.
Bernet et al. "Lactobacillus Acidophilus LA 1 Binds to Cultured Human Intestinal Cell Lines and Inhibits Cell Attachment and Cell Invasion by Enterovirulent Bacteria." *Gut* 35.4(1994):483-489.
Bilsborough et al., "A review of issues of dietary protein intake in humans". Int J Sport Nutr Exerc Metab. Apr. 2006;16(2):129-52.

Black et al. "Experimental *Camplylobacter jejuni* Infection in Humans." *J. Infect. Dis.* 157.3(1988):472-479.
Blaser et al. "The Influence of Immunity on Raw Milk-Associated Campylobacter Infection." *JAMA.* 257.1 (1987):43-46.
Blaser. "Campylobacter Species." *Principles and Practice of Infectious Diseases.* Mandell et al.,eds. New York: Churchill Livingstone Inc. 3(1990):1649-1658.
Blum et al. "Improved Silver Staining of Plant Proteins, RNA and DNA in Polyacrylamide Gels." *Electrophoresis.* 8.1(1987):93-99. (Abstract Only).
Bush et al. "High-Level Penicillin Resistance Among Isolates of Enterococci: Implications for Treatment of Enterococcal Infections." *Ann. Intern. Med.* 110.7(1989):515-520. (Abstract Only).
Castellazzi et al. "In vitro Activation of Mononuclear Cells by Two Probiotics: *Lactobacillus paracasei* I 1688, *Lactobacillus salivarius* I 1794, and their Mixture (PSMIX)." *Immunological Invest.* 36.4(2007):413-421.
Challa et al. "*Bifidobacterium longum* and Lactulose Suppress Azoxymethane-Induced Colonic Aberrant Crypt foci in Rats." *Carcinogenesis.* 18.3(1997):517-521.
Chandra et al. "Effect of *Lactobacillus* on the Incidence and Severity of Acute Rotavirus Diarrhoea in Infants." *Nut. Res.* 22.1-2(2002):65-69.
Choi et al. "Fructose Intolerance: An Under-Recognized Problem." *Am. J. Gastroenterol.* 98.6(2003):1348-1353.
Christi et al. "Role of Dietary Sulphate in the Regulation of Methanogenesis in the Human Large Intestine." *Gut.* 33.9(1992):1234-1238.
Clark et al. "Characterization of Glycopeptide-Resistant Enterococci From U.S. Hospitals." *Antimicrob. Agents Chemother.* 37.11 (1993):2311-2317.
Clausen et al. "Functional Significance of the Activation-Associated Receptors CD25 and CD69 on Human NK-Cells and NK-like T-Cells." *Immunobiol.* 207.2(2003):85-93.
Clewell et al. "Conjugative Transposons and the Dissemination of Antibiotic Resistance in Strepococci." *Annu. Rev. Microbiol.* 40(1986):635-659.
Clewell et al. "Sex Pheromones and Plasmid Transfer in *Enterococcus faeclis.*" *Plasmid.* 21.3(1989):175-184. (Absract Only).
Clewell. "Plasmids, Drug Resistance, and Gene Transfer in the Genus *Streptococcus.*" *Microbiol. Rev.* 45.3(1981 ):409-436.
Cometta et al. "*Escherichia coli* Resistant to Fluoroquinolones in Patients with Cancer and Neutropenia." *New Engl. J. Med.* 330. 17(1994):1240-1241.
Cross et al. "Patterns of Cytokine Induction by Gram-Positive and Gram-Negative Probiotic Bacteria." *FEMS Immunol. Med. Microbiol.* 42.2(2004):173-180.
Cui et al. "Efficacy of Bacillus coagulans Tablets in the Treatment of Acute and Chronic Diarrhea." *Int. J. Immunother.* 20.1(2004):17-22.
Database WPI, Section Ch, Week 198918, Derwent Publications Ltd., AN 1989-136223 XP002130556 & JP 01 083025 A (Hayashi), Mar. 28, 1989. (Abstract Only).
Database WPI, Section Ch, Week 199637, Derwent Publications Ltd., AN 1996-368043 XP002130557 & JP 08 175921 A (Idemitsu Kosan Co., Ltd.), Jul. 9, 1996, (Abstract Only).
De Simone et al. "Effect of *Bifidobacterium bifidum* and *Lactobacillus acidophilus* on Gut Mucosa and Peripheral Blood B Lymphocytes." *Immunopharmacol. Immunotoxicol.* 14.1&2(1992):331-340.
De Vecchi et al. "*Lactobacillus Sporogenes* or *Baccillus Coagulans*: Misidentification or Mislabelling?" *Int. J. Probiotics Probiotics.* 1.1(2006):3-10.
De Vrese et al. "Probiotic Bacteria Reduced Duration and Severity but not the Incidence of Common Cold Episodes in a Double Blind, Randomized, Controlled Trial." *Vaccine.* 24(2006):6670-6674.
Devriese et al. "Phenotypic Identification of the Genus *Enterococcus* and Differentiation of Phylogenetically Distinct Enterococcal Species and Species Groups." *J. Appl. Bacteriol.* 75.5(1993):399-408.(Abstract Only).
DSM No. 2356, Bacillus coagulans Hammer 1915 emend. De Clerck et al., 2004 (NCIB 8523).

(56) References Cited

OTHER PUBLICATIONS

El-Baz. "Herbal and Floral Teas, Infusions, or Tisanes?" *The Essence of Herbal and Floral Teas*. New York: iUniverse. (2006):1-5.
Eliopoulos et al. "In Vitro Activities of Two Glycylcyclines Against Gram-Positive Bacteria." *Antimicrob. Agents Chemother*. 38.3(1994):534-541.
Elmer et al. "A Neglected Modality for the Treatment and Prevention of Selected Intestinal and Vaginal Infections." *JAMA*. 275(1996):870-876.
*Enzyme Nomenclature*. New York: Academic Press. (1984):602.
Evans et al. "Fructose-Sorbitol Malabsorption and Symptom Provocation in Irritable Bowel Syndrome: Relationship to Enteric Hypersensitivity and Dysmotility." *Scandinavian J. Gastroenterol*. 33.11 (1998):1158-1163.
Famularo et al. "Stimulation of Immunity by Probiotics." *Probiotics 2: Applications and Practical Aspects*. Fuller, ed. London: Boundary Row. (1997):133-161.
Farmer et al. "Bacillus coagulans. Cholesterol: Fact and Theory." *Empower*. 1.3(1998):8, 38-41.
Farmer et al. "The Only GRAS-Listed Bacillus Probiotic." *Empower*. (1997):5-7, 42-43.
Fernandez et al. "Effect of Diatomaceous Earth as an Anthelnimtic Treatment on Internal Parasites and Feedlot Performance of Beef Steers." *Animal Science* 66.3(1998): 635-641.
Fink et al. "Intestinal Gas." *Curr. Treat. Options Gastronenterol*. 4.4(2001 ):333-337.
Flinterman et al. "Probiotics Have a Different Immunomodulatory Potential in vitro versus ex vivo Upon Oral Administration in Children With Food Allergy." *Intl. Arch. Allergy Immunol*. 143. 3(2007):237-244.
*Food Chemicals Codex*. Washington, D.C.: National Academy Press. 3rd ed.(1981):491-492.
Friend et al. "Nutritional and Therapeutic Aspects of Lactobacilli." *J. Appl. Nutr*. 36.2(1984):125-153.
Fukushima et al. "The Effect of a Probiotic on Faecal and Liver Lipid Classes in Rats." *Br. J. Nutr*. 73.5(1995):701-710.
Fuller, R., "A Review: Probiotics in man and animals", J. Appl. Bacteriol., 66:365-378 (1989).
Fuller. "History and Development of Probiotics." *Probiotics: the Scientific Basis*. Fuller, ed. London: Chapman & Hall. Chapter One(1992):1-8.
Gandhi. "Lactobacillus sporogenese: An Advancement in Lactobacillus Therapy." Townsend Lett. Doctors Patients. 150(1996):108-110.
Ganedenbc30, 2012 press release, (www.ganedenbc30.com/news_and_ events/press_release/new-study-demonstrates..).
Giardin et al., "Antimicrobial Activity of Foodborne *Paenibacillus* and *Bacillus* spp. Against Clostridium botulinum", J. Food Protection, 62(5):806-813 (2002) (Abstract Only).
Gibson et al. "Selective Stimulation of Bifidobacteria in the Human Colon by Oligofructose and Insulin." *Gastroenterol*. 108(1995):975-982.
Goldstein et al. "Carbohydrate Malabsorption and the Effect of Dietary Restriction on Symptoms of Irritable Bowel Syndrome and Functional Bowel Complaints." *Isr. Med. Assoc. J*. 2.8(2000):583-587.
Gorbach. "Lactic Acid Bacteria and Human Health." Ann. Med. 22(1990):27-41.
Hata et al. "Meningitis Caused by *Bifidobacterium* in an Infant." *Pediatr. Infect. Dis*. 7(1988):669-671.
Hill et al. "Vaginitis: Current Microbiologic and Clinical Concepts." *Can. Med. Assoc. J*. 134(1986):321-331.
Hiramatsu et al. "Methicillin-Resistant *Staphylococcus aureus* Clinical Strain With Reduced Vancomycin Susceptibility." *J. Antimicrob. Chemother*. 40.1(1997):135-136.
Horodniceanu et al. "High-Level, Plasmid-Borne Resistance to Gentamicin in *Streptococcus faecalis* Subsp. Zymogenes." *Antimicrob. Agents Chemother*. 16.5(1979):686-689.
Hugenholtz. "Citrate Metabolism in Lactic Acid Bacteria." *FEMS Microbiol. Rev*. 12(1993):165-178.
Hughes et al. "Identification of Immobilized Bacteria by Aminopeptidase Profiling." *Anal. Chem*. 61.15(1989):1656-1660. (Abstract Only).
Hun. "Original Research: *Bacillus coagulans* Significantly Improved Abdominal Pain and Bloating in Patients with IBS." *Postgrad. Med*. 121.2(2009):119-124.
Hyronimus et al. "Acid and Bile Tolerance of Spore-Forming Lactic Acid Bacteria." *Int. J. Food Microbiol*. 61.2-3(2000):193-197. (Abstract Only).
Hyronimus et al. "Coagulin, a Bacteriocin-Like Inhibitory Substance Produced by Bacillus Coagulans I4." *J. Appl. Microbiol*. 85.1(1998):42-50.
International Search Report for PCT/US05/16469, dated Dec. 5, 2005.
Jacobs-Reitsma et al. "The Induction of Quinolone Resistance in *Campylobacter* Bacteria in Broilers by Quinolone Treatment." *Campylobacter, Helicobacters, and Related Organisms*. Newell et al., eds. NewYorkL Plenum Press. (1996):307-311.
Jensen et al. "An Antiinflammatory Immunogen From Yeast Culture Induces Activation and Alters Chemokine Receptor Expression on Human Natural Killer Cells and B Lymphocytes in vitro." *Nutr. Res*. 27.6(2007):327-335.
Jensen et al. "GanedenBC$^{30}$™ Cell Wall and Metabolites: Anti-Inflammatory and Immune Modulating Effects in vitro." *BMC Immunol*. 11(2010):15.
Kaya et al. "Structural Studies on the Linkage Unit Between Poly(galactosylglycerol phosphate) and Peptidoglycan in Cell Walls of *Bacillus coagulans*." *Eur. J. Biochem*. 147(1985):41-46.
Ketley. "Pathogenesis of Enteric Infection by *Campylobacter*." *Microbiol*. 143(1997):5-21.
Kim et al. "Bacillus Coagulans ORF17 Strain Resistance to Rifampicin and Ofloxacin." *Yakhak Hoeji (J. Pharm. Soc. Korea)*. 41.4(1997):450-455. (English Language Translation of Abstract Only).
Kim et al. "Development of Lactobacillus-Sporogenes Resistant to Rifampicin an Antituberculosis Agent." Korean J. Micro. 27.2(1989):155-161. (Abstract Only).
Klaenhammer. "Genetics of Bacteriocins Produced by Lactic Acid Bacteria." *FEMS Microbial. Rev*. 12(1993):39-85.
Koo et al. "Long-Term Effect of Bifidobacteria and Neosugar on Precursor Lesions of Colonic Cancer in Cf.sub.1 Mice." Nutrit. Rev. 16(1991):249-257.
Korshunov et al. "Effect of the Combined Administration of Antibiotic Resistant Bifidobacteria and the Corresponding Antibiotics on the Survival of Irradiated Mice." *Zh. Mikrobiol. Epidemol. Immunobiol*. 5(1982):50-53. (English Language Translation of Abstract Only).
Kreuzer, M., "Probiotic-antibiotic interactions in performance, intestinal fermentation and manure properties of piglets using a Bacillus (B. licheniformis/B. subtilis) preparation and Carbadox", Agribiol. Res., 47(1):13-23 (1994).
La Rosa et al. "Prevention of Antibiotic-Associated Diarrhea With *Lactobacillus sporogens* and Fructo-Oligosaccharides in Children." *Minerva Pediatrica*. 55.5(2003):447-452. ( Abstract Only).
Laemmli. "Cleavage of Structural Proteins during the Assembly of the Head of Bacteriophage T4." *Nature*. 227(1970):680-685.
Lidbeck et al. "Lactobacilli, Anticarcinogenic Activities and Human Intestinal Microflora." *Eur. J. Cancer Prev*. 1.5(1992):341-354.
Lieberman et al., Pharmaceutical Dosage Forms—Tablets , vol. 3, Marcel Dekker, Inc., New York, NY, pp. 114-116 (1990).
Lino et al. "A Study on the Effect of Bacillus coagulans, a Spore-Forming Lactic Acid Bacteria, in Improving the Properties of Feces." Prog. Med. 17(1997):3299-3302.
Malin et al. "Promotion of IgA Immune Response in Patients with Crohn's Disease by Oral Bacteriotherapy with Lactobacillus GG." *Ann. Nutr. Metab*. 40(1996):137-145.
Marsh, "Antimicrobial Strategies in the Prevention of Dental Caries", Caries Res., (1993) 27:72-76.
Maathuis AJ, et al., Survival and metabolic activity of the GanedenBC30 strain of Bacillus coagulans in a dynamic in vitro model of the stomach and small intestine. Benef Microbes. Mar. 2010;1(1):31-6.
Matsumara et al. "Interferon Induction by Murine Peritoneal Macrophage Stimulated with *Lactobacillus gasseri*." *Animal Sci. Technol. (Jpn)*. 63(1992):1157-1159.

(56) References Cited

OTHER PUBLICATIONS

Max Muscle, Product Datasheet ,www.maxmuscle.com, Retrieved Oct. 29, 2015.
Metchinikoff. "Longevity in the Animal Kingdom." *Prolongation of Life.* New York: The Knickerbocker Press. (1910):39-93, 132-183. Microbax-:web.archive.org/web/200006040357471http://www.microbax.co-m/product.htm)(accessed Jul. 22, 2008.
Mitchell. "Rearming in the Fight Against Bacteria." *Lancet.* 352(1998):462.
Yamashita et al. "Effects of Fructo-oligosaccharides on Blood Glucose and Serum Lipids in Diabetic Subjects." *Nutr. Res.* 4(1984):961-966.
Mohan et al. "Preliminary Observations on Effect of Lactobacillus sporogenes on Serum Lipid Levels in Hypercholesterolemin Patients." *Indian J. Med. Res.* 92(1990):431-432.
Molin et al. "Effect of Fermented Oatmeal Soup on te Cholesterol Level and Lactobacillus Colonization of Rat Intestinal Mucosa." *Antonie Van Leeuwenhoek.* 61.3(1992):167-173.
Montecalvo et al. "Outbreak of Vancomycin-, Ampicillin-, and Aminoglycoside-Resistant Enterococcus faecium Bacteremia in an Adult Oncology Unit." *Antimicrobiol. Agents Chemother.* 38(1994):1363-1367.
Mossman et al. "Aminopeptidase Profiling Using a Time-Resolved, 96-Well Plate Filter Fluorimeter." *Appl. Spectroscopy.* 51.10(1997):1443-1446.( Abstract Only).
Murphy et al. "Ciprofloxacin- and Azithromycin-Resistant Campylobacter Causing Traveler's Diarrhea in U.S. Troops Deployed to Thailand in 1994." *Clin. Infect. Dis.* 22(1996):868-869.
Mustapha et al. "Improvement of Lactose Digestion by Humans Following Ingestion of Unfermented Acidophilus Milk: Influence of Bile Sensitivity, Lactose Transport, and Acid Tolerance of Lactobacillus acidophilus." *J. Dairy Sci.* 80(1997):1537-1545.
Nairn. "Solutions, Emulsions, Suspensions and Extracts." *Remington's 18th Ed.* Easton, PA: Mack Publishing Co. Chapter 83(1990):1519-1544.
Nakamura et al. "Taxonomic Study for Bacillus coagulans Hammer 1915." J. Systematic Bacterio. 38(1988):63-73.
Ng et al. "Mechanisms of Action of Probiotics: Recent Advances." *Inflammatory Bowel Dis.* 15.2(2009):300-310.
Noble et al. "Co-Transfer of Vancomycin and Other Resistance Genes From *Enterococcus faecalis* NCTC 12201 to *Staphylococcus aureus.*" *FEMS Microbiol. Lett.* 93.2(1992):195-198.
Oyarzabal et al. "In vitro Fructooligasaccharide Utilization and Inhibition of *Salmonella* spp. By Selected Bacteria." *Poultry Sci.* 74.9(1995):1418-1425.
Palop et al. "Occurrence of a Highly Heat-Sensitive Spore Subpopulationof Bacillus Coagulans STCC 4522 and its Conversion to a More Heat-Stable Form." *Appl. Environ. Microbiol.* 63.6(1997):2246-2251.
Panda et al. "Effect of Probiotic (*Lactobacillus sporogenes*) Feeding on Egg Production and Quality, Yolk Cholesterol and Humoral Immune Response of White Leghorn Layer Breeders." *J. Sci. Food Agricul.* 88.1(2008):43-47.
Perdigon et al. "Symposium: Probiotic Bacteria For Humans: Clinical Systems for Evaluation of Effectiveness. Immune System Stimulation by Probiotic." *J. Dairy Sci.* 78(1995):1597-1606.
Perlman et al. "Persistent Campylobacter jejuni Infections in Patients Infected with Human Immunodeficiency Virus (HIV)." *Ann. Intern. Med.* 108(1988):540-546.
Peterson. "Conference and Review: Clinical Aspects of Campylobacter jejuni Infections in Adults." *Wes. J. Med.* 161.2(1994):148-152.
Peterson. "Rheumatic Manifestations of *Campylobacter jejuni* and *C. fetus* Infections in Adults." *Scand. J. Rheumatol.* 23(1994):167-170.
Piard et al. "Inhibiting Factors Produced by Lactic Acid Bacteria. 1. Oxygen Metabolites and Catabolism End-Products." *Lait.* 71(1991):525-541.
Piddock. "Quinolone Resistance and *Campylobacter* spp." *J. Antimicrob. Chemother.* 36(1995):891-898.

Quale et al. "Manipulation of a Hospital Antimicrobial Formulary to Control an Outbreak of Vancomycin-Resistant Enterococci." *Clin. Infect. Dis.* 23.5(1996):1020-1025.
Rafter et al. "The Role of Lactic Acid Bacteria in Colon Cancer Prevention." *Scand. J. Gastroenterol.* 80(1995):497-502.
Reddy et al. "Inhibitory Effect of *Bifidobacterium longum* on Colon, Mammary, and Liver Carcinogenesis Indued by 2-Amino-3-Methylimidazo[4,5-f]quinoline, a Food Mutagen." *Cancer Res.* 53.17(1993):3914-3918.
Reid et al. "Is There a Role for Lactobacilli in Prevention of Urogenital and Intestinal Infections?" *Clin. Microbiol. Rev.* 3.4(1990):335-344.
Riazil, S. et al., "Characterization of lactosporin, a novel antimicrobial protein produced by Bacillus coagulans ATCC 7050," J. Appl. Microbiol., vol. 106.4 (2009):1370-1377.
Rice et al. "Occurrence of High-Level Aminoglycoside Resistance in Environmental Isolates of Enterococci." *Appl. Environ. Microbiol.* 61.1(1995):374-376.
Roberts. "Characterization of the Tet M Determinants in Urogenital and Respiratory Bacteria." *Antimicrob. Agents Chemother.* 34.3(1990):476-478.
Rowland et al. "Degradation of N-Nitrosamines by Intestinal Bacteria." *Appl. Microbiol.* 29(1975):7-12.
Rudnic et al. "Oral Solid Dosage Forms." *Remington's 18th Ed.* Easton, PA: Mack Publishing Co. Chapter 89(1990):1633-1665.
Rychen et al. "Effects of Three Microbial Probiotics on Postprandial Porto-Arterial Concentration Differences of Glucose, Galactose and Amino-Nitrogen in the Young Pig." *Brit. J. Nutr.* 74(1995):19-26.
Saavedra et al. "Feeding of Bifidobacterium bifidum and *Streptococcus thermophilus* in Infants in Hospital for Prevention of Diarrhea and Shedding of Rotavirus." *Lancet.* 344(1994):1046-1049.
Sahm et al. "In Vitro Susceptibility Studies of Vancomycin-Resistant Enterococcus faecalis." *Antimicrob. Agents Chemother.* 33.9(1989):1588-1591.
Saitou et al. "The Neighbor-Joining Method: A New Method for Reconstructing Phylogenetic Trees." *Mol. Biol. Evol.* 4.4(1987):406-425.
Salimen et al. "Clinical Uses of Probiotics for Stabilizing the Gut Mucosal Barrier: Successful Strains and Future Challenges." *Antonie Van Leeuwenhoek.* 70.2-4(1996):347-358.
Salminen et al. "Functional Food Science and Gastrointestinal Physiology and Function." *Br. J. Nutr.* 80.S1(1998):S147-S171.
Sanders et al. "Sporeformers as Human Probiotics: *Bacillus, Sporolactobacillus,* and *Brevibacillus.*" *Comprehensive Rev. Food Sci. Food Safety.* 2(2003):101-110.
Sapico et al. "Enterococci Highly Resistant to Penicillin and Ampicillin: An Emerging Clinical Problem?" *J. Clin. Microbiol.* 27.9(1989):2091-2095.
Schaafsma et al. "Effects of a Milk Product, Fermented by Lactobacillus acidophilus and With Fructo-ogliosaccharides Added, on Blood Lipids in Male Volunteers." *Eur. J. Clin. Nutr.* 52.6(1998):436-440. (Abstract Only).
Schiffrin et al. "Immune Modulation of Blood Leukocytes in Humans by Lactic Acid Bacteria: Criteria for Strain Selection." *Am. J. Clin. Nutr.* 66(1997):515S-520S.
Sekine et al. "Induction and Activation of Tumoricidal Cells In Vivo and In Vitro by the Bacterial Cell Wall of Bifdobacterium infantis." *Bifidobact. Microflora.* 13(1994):65-77.
Shannon et al. "Multiple-Antibiotic-Resistant *Salmonella.*" *Lancet.* 352(1998):490.
Shoenfeld et al. "Guillain-Barré as an Autoimmune Disease." *Int. Arch. Allergy Immunol.* 109(1996):318-326.
Singh et al. "Stevia: The Herbal Sugar of 21st Century." *Sugar Technology.* 7.1 (2005):17-24.
Smith et al. "Fluoroquinolone-Resistant Campylobacter Isolated from Humans and Poultry in Minnesota." *Int. Conf. Emerging Infect. Dis.* Mar. 8-11, 1998:69.
Sneath et al., eds. *Bergey's Manual of Systematic Bacteriology.* Baltimore: Williams & Wilkins. 2(1984):1117.
Solis-Pereyra et al. "Induction of Human Cytokines by Bacteria Used in Dairy Foods." *Nutr. Res.* 13(1993):1127-1140.
Somogyi. "Modifications of Two Methods for the Assay of Amylase." *Clin. Chem.* 6.1 (1960):23-35.

(56) References Cited

OTHER PUBLICATIONS

Sorvillo et al. "Incidence of Campylobacteriosis Among Patients with AIDS in Los Angeles County." *J. Acquired Immune Defic. Syndr.* 4(1991):598-602.

Stackebrandt et al. "Taxonomic Note: A Place for DNA-DNA Reassociation and 16S rRNA Sequence Analysis in the Present Species Definition in Bacteriology." *Int. J. Syst. Bacteriol.* 44.4(1994):846-849. (Abstract Only).

Standiford et al. "Lipoteichoic Acid Induces Secretion of Interleukin-8 from Human Blood Monocytes: a Cellular and Molecular Analysis." *Infect. Immun.* 62.1 (1994):119-125.

Sussman et al. "Clinical Manifestations and Therapy of Lactobacillus endocarditis: Report of a Case and Review of the Literature." *Rev Infect. Dis.* 8(1986):771-776.

Suzuki et al. "Purification and Characterization of *Bacillus coagulans* Oligo-1,6-Glucosidase." *Eur. J. Biochem.* 158.1(1986):77-83.

Tauxe. "Epidemiology of Campylobacter jejuni Infections in the United States and Other Industrial Nations." Campylobacter jejuni. Nachamkin et al., eds. Washington, DC: American Society for Microbilogy. (1992):9-13.

Thomason et al. "Bacterial Vaginosis: Current Review with Indcations for Asymptomatic Therapy." *Am. J. Obstet. Gynecol.* 165. 4(1991 ):1210-1217.

Thompson et al. "Functional Bowel Disorders and Functional Abdominal Pain." *Gut.* 45.S2(1999):II43-II47.

Thompson et al. "Irritable Bowel Syndrome: Guidelines for the Diagnosis." *Gastroenterol. Int.* 2.2(1989):92-95.

Tietz et al. "A Specific Method for Serum Lipase Determination." *Clin. Chim. Acta.* 13.3(1966):352-358.

Tojo et al. "The Effects of Bifidobacterium Breve Administration on Campylobacter Enteritis." *Acta Paediatr. Jpn.* 29.1 (1987):160-167.

Waterman. *Introduction to Computational Biology: Maps, Sequences and Genomes.* New York: Chapman &Hall CRC. (1995):360-365.

Winberg et al. "Pathogenesis of Urinary Tract Infection—Experimental Studies of Vaginal Resistance to Colonization." *Pediatr. Nephrol.* 7(1993):509-514.

Windholz et al., eds. The Merck Index. 10(1983):549.

Yamazaki et al. "Protective Effect of Bifidobacterium Monoassociation Against Lethal Activity of *Escherichia coli.*" *Bifidobacteria Microflora.* 1(1982):55-59.

Yanagida et al. "Morphological, Biochemical, and Physiological Characteristics of Spore Forming Lactic Acid Bacteria." *J. Gen. Appl. Microbiol.* 33(1987):33-45.

Zervos et al. "Nosocomical Infection by Gentamicin-Resistant *Streptococcus faecalis*: An Epidemiologic Study." *Ann. Intern. Med.* 106.5(1987):687-691. (Abstract Only).

Zhang et al. "Antimutagenicity and Binding of Lactic Acid Bacteria From a Chinese Cheese to a Mutagenic Pyrolyzates." *J. Dairy Sci.* 73.10(1990):2702-2710.

Zhou et al. "Effect of Treatment With Probiotics as Water Additives on Tilapia (*Oreochromis niloticus*) Growth Performance and Immune Response." *Fish Physiol. Biochem.* 36.3(2009):501-509.

Ziemer et al. "An Overview of Probiotics, Prebiotics and Symbiotic in the Functional Food Concept: Perspectives and Future Strategies." *Int. Dairy J.* 8(1998):473-479.

Sealey et al. (2009) "Soybean meal level and probiotics in first feeding fry diets alter the ability of rainbow trout *Oncorhynchus mykiss* to utilize high levels of soybean meal during grow-out", Aquaculture, 293(3-4): 195-203.

\* cited by examiner

PROBIOTIC SPORTS NUTRITION COMPOSITIONS

RELATED APPLICATIONS

This application claims the benefit of priority under 35 U.S.C. § 119(e) to U.S. Provisional Application No. 61/469,924, filed Mar. 31, 2011, which is incorporated herein by reference in its entirety.

FIELD OF THE INVENTION

The present application relates to sports nutrition compositions comprising lactic acid-producing bacteria.

BACKGROUND OF THE INVENTION

The gastrointestinal microflora plays a number of vital roles in maintaining gastrointestinal tract function and overall physiological health. The growth and metabolism of the many individual bacterial species inhabiting the gastrointestinal tract depend upon the substrates available to them, most of which are derived from the diet.

Probiotic organisms are non-pathogenic, non-toxigenic microorganisms that are beneficial to the host organism. Since probiotics do not generally permanently colonize the host, they are typically ingested regularly for health promoting properties to persist.

SUMMARY OF THE INVENTION

The invention is based on the discovery that lactic acid-producing bacteria, particularly *Bacillus coagulans*, improve the absorption of protein compositions as well as micronutrient compositions. The microorganisms, e.g., spores remain viable, retain their beneficial probiotic properties, and increase metabolism and/or absorption of protein in sports nutrition compositions. Unlike other probiotic bacteria that die in the stomach or small intestine, the probiotic organisms described herein, e.g., *Bacillus coagulans* strain GBI-30 or BC$^{30}$, ATCC Designation Number PTA-6086, germinate in the stomach and/or small intestine. Accordingly, the invention describes probiotic sports nutrition compositions. The invention provides an isolated *Bacillus coagulans* bacterium (e.g., a spore) in sports nutrition compositions. In some cases, the composition comprises at least 15% protein. For example, the composition comprises at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99% or more of a purified or processed protein (e.g., protein extracted from a food-stuff) and a *Bacillus coagulans* spore.

The compositions described herein are suitable for consumption by a mammal, e.g., any mammal, e.g., a human, a primate, a mouse, a rat, a dog, a cat, a cow, a horse, or a pig. In a preferred embodiment, the mammal is a human. For example, the invention includes a method of enhancing lean muscle development or increasing lean body mass by administering to a subject a composition comprising a *Bacillus coagulans* spore in a composition comprising at least 85% purified, processed, and/or isolated protein. The subject is a human being that desires to increase muscle development, strength, or lean body mass, or an animal, e.g., livestock or performance animal such as a work animal or a race horse, for which an increase in muscle development or strength is desired. The compositions are also useful to confer clinical benefit to individuals that are suffering from or at risk of developing a muscle wasting condition, e.g., cachexia, as a result of disease such as cancer or infection.

The invention provides a composition comprising a sports nutrition composition and an isolated *Bacillus coagulans* spore (e.g., in an amount of 1×10$^6$ to 1×10$^{14}$ colony forming units (CFU) of *Bacillus coagulans* per unit dose. For example, the isolated *Bacillus coagulans* comprise between about 0.000001% to about 50% by weight of the composition, e.g., about 1%, about 10%, about 20%, about 30%, about 40%, or about 50% by weight of the composition. For example, the isolated *Bacillus coagulans* comprise between about 0.00001% and about 25% by weight of the composition, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight of the composition. In one example, one unit dose, e.g., one serving, comprises one billion CFU *Bacillus coagulans* and 20-25 grams of protein (e.g., 23 grams of whey protein) in 30 grams of powder. The balance of the composition optionally comprises nutritionally inactive ingredients such as excipients, fillers, preservatives or nutritionally active ingredients such as vitamins or minerals.

The invention also provides bacterial species including *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or BC$^{30}$, ATCC Designation Number PTA-6086; and GBI-40, ATCC Designation Number PTA-6087; see U.S. Pat. No. 6,849,256 to Farmer).

Optionally, the isolated *Bacillus coagulans* is in the form of a spore. Alternatively, the isolated *Bacillus coagulans* is in the form of a vegetative cell. In another aspect, the isolated *Bacillus coagulans* is in the form of a mixture of vegetative cells and spores. The *Bacillus coagulans* is predominantly in spore form, e.g., about 75%, about 80%, about 85%, about 90%, about 95%, about 96%, about 97%, about 98%, about 99%, or about 100% spores. Alternatively, the *Bacillus coagulans* is predominantly in vegetative form, e.g., about 75%, about 80%, about 85%, about 90%, about 95%, about 96%, about 97%, about 98%, about 99%, or about 100% vegetative cells.

Provided is an isolated *Bacillus coagulans* and a sports nutrition composition. In some cases, the compositions described herein comprise a large amount of calories per unit dose to assist a subject in gaining weight, e.g., muscle weight or fat weight. A unit dose of the compositions described herein is the amount of composition administered to a consumer in a single dose, i.e., one serving. Unit-dose packaging is the packaging of a single dose, e.g., in a non-reusable container. For example, a unit dose refers to a physically discrete unit suitable as unitary dosages for an individual, each unit containing a predetermined quantity of active material calculated to produce the desired therapeutic effect, in association with a suitable pharmaceutical carrier, diluent, or excipient. Suitable packaging includes single or multiple unit dosages.

Compositions that provide a large amount of calories to assist a subject in gaining weight are referred to as "weight gainers." In these cases, the composition comprises between about 100 and about 10,000 food Calories (kcal) per unit dose (i.e., serving), e.g., between 250 and 5,000 kcal, between 500 and 3,000 kcal, between 750 and 2,500 kcal, or between 1,000 and 2,000 kcal, e.g., about 1,000 kcal, about 1,100 kcal, about 1,200 kcal, about 1,300 kcal, about 1,400 kcal, about 1,500 kcal, about 1,600 kcal, about 1,700 kcal, about 1,800 kcal, about 1,900 kcal, or about 2,000 kcal. One exemplary amount of calories is 1,230 kcal. Alternatively, the compositions do not comprise a large amount of calories. For example, the compositions comprise between about 10 and 500 kcal, e.g., between about 20 and 250 kcal, between about 50 and 200 kcal, or between about 100 and 150 kcal, e.g., about 100 kcal, about 110 kcal, about 120 kcal, about 130 kcal, about 140 kcal, or about 150 kcal. One exemplary amount of calories is about 150 kcal.

Preferably, the composition comprises protein. For example, the protein comprises about 1% to about 99% by weight of the composition, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% by weight of the composition. For example, the composition comprises between 1 gram and 500 grams of protein, e.g., about 10 grams, about 15 grams, about 20 grams, about 25 grams, about 30 grams, about 35 grams, about 40 grams, about 45 grams, about 50 grams, about 55 grams, about 60 grams, about 65 grams, about 70 grams, about 75 grams, about 80 grams, about 85 grams, about 90 grams, about 95 grams, about 100 grams, about 150 grams, about 200 grams, about 250 grams, about 300 grams, about 350 grams, about 400 grams, about 450 grams, or about 500 grams of protein. One exemplary composition comprises about 62% protein. For example, the composition comprises about 39 total grams, of which about 24 grams is protein. Another exemplary composition comprises about 65% protein. For example, the composition comprises about 31 total grams, of which about 20 grams is protein. Another exemplary composition comprises about 15% protein. For example, the composition comprises about 325 total grams, of which about 50 grams is protein. A typical protein composition comprises about 50-100% protein such as whey protein. For example, a unit dose comprises 1 billion CFU of *Bacillus coagulans* and 23 grams of whey protein in a total of 30 grams of powder.

In one aspect, the sports nutrition composition comprises purified or processed protein, such as soy protein, whey protein, rice protein, hemp seed protein, casein protein or milk protein. Preferably, the protein comprises whey protein. The protein comprises an amino acid selected from the group consisting of isoleucine, alanine, leucine, arginine, lysine, aspartate, aspartic acid, methionine, cysteine, phenylalanine, threonine, tryptophan, glycine, valine, proline, histidine, serine, tyrosine, asparagine, selenocysteine, pyrrolysine, glutamate, glutamic acid, and glutamine. Optionally, the sports nutrition composition comprises an isolated *Bacillus coagulans* and protein, and further comprises creatine, calcium, sodium caseinate, whey peptides, or lactoferrin. Alternatively, the invention provides an isolated *Bacillus coagulans* and a sports nutrition composition selected from the group consisting of creatine, calcium, sodium caseinate, whey peptides, and lactoferrin.

The compositions optionally further comprise additional ingredients selected from the group consisting of sodium, potassium, sugar, carbohydrates, dietary fiber, vitamin A, vitamin C, calcium, iron, vitamin D, vitamin E, thiamin, riboflavin, niacin, vitamin B6, folate, vitamin B12, biotin, pantothenic acid, phosphorus, iodine, magnesium, zinc, selenium, copper, manganese, chromium, and molybdenum.

An exemplary composition comprises glucose polymer, a protein blend (i.e., whey protein concentrate, whey protein isolate, egg albumin, milk protein isolate, and partially hydrolyzed whey protein), rice protein concentrate, brown rice concentrate, taurine, L-glutamine, non-dairy creamer (i.e., sunflower oil, corn syrup solids, sodium caseinate, mono- and diglycerides, dipotassium phosphate, tricalcium phosphate, soy lecithin, and tocopherols), natural and artificial flavors, xantham gum, calcium citrate, potassium citrate, dipotassium phosphate, cellulose gum, tricalcium phosphate, magnesium aspartate, rice starch, carrageenan, vitamin-mineral blend (i.e., ascorbic acid, niacinamide, d-Alpha tocopheryl succinate, d-calcium pantothonate, zinc citrate, pyridoxine hydrochloride, ferrous fumarate, thiamine mononitrate, riboflavin, manganese amino acid chelate, beta-carotene, copper gluconate, folic acid, biotin, potassium iodide, chromium polynicotinate, molybdenum amino acid chelate, selenomethionine, cyanocobalamin, and cholecalciferol), GANEDEN BC-30™ (*Bacillus coagulans* GBI-30, ATCC Designation Number PTA-6086), sucralose, acesulfame potassium, and lactase.

Another exemplary composition comprises the following ingredients: whey protein concentrate, brown rice protein concentrate, whey protein isolate, egg albumin, milk protein isolate, partially hydrolyzed whey protein, glucose polymer, taurine, L-glutamine, nondairy creamer (i.e., sunflower oil, corn syrup solids, sodium caseinate, mono- and diglycerides, dopotassium phosphate, tricalcium phosphate, soy lecithin, and tocopherols), dicalcium phosphate, natural and artificial flavors, xanthan gum, cellulose gum, carrageenan, lecithin, acesulfame potassium, sucralose, lactase, and GANEDEN BC-30™ (*Bacillus coagulans* GBI-30, ATCC Designation Number PTA-6086).

The compositions contain active ingredients, e.g., protein and GANEDEN BC-30™ (*Bacillus coagulans* GBI-30, ATCC Designation Number PTA-6086), and inactive ingredients, e.g., excipients, binders, or fillers. Fillers fill out the size of the compositions, making it practical to produce and convenient for the consumer to use. By increasing the bulk volume, the fillers make it possible for the final product to have the proper volume for consumer handling. Suitable fillers include xantham gum, cellulose gum, lecithin, lactose, sucrose, glucose, mannitol, sorbitol, calcium carbonate, and magnesium stearate.

In some cases, the compositions do not comprise certain ingredients. For example, the composition does not include a sugar (e.g., glucose, fructose, galactose, maltose or lactose), gluten, aspartame, and/or artificial coloring.

Exemplary forms for the compositions described herein include a protein powder, a ready to drink protein shake, a protein bar, a protein bite, and a protein gel.

The invention provides compositions comprising a dry mix for sports nutrition compositions comprising an isolated *Bacillus coagulans* bacterium and a sports nutrition composition. The dry mix is between 0.01% and 50% *Bacillus coagulans* bacterium, e.g., about 1%, about 5%, about 10%, about 15%, about 20%, about 25%, about 35%, about 45%, or about 50% *Bacillus coagulans* bacterium. In some cases, the dry mix is about 15% *Bacillus coagulans* bacterium. For example, about 100 pounds of dry mix contains about 15 pounds of *Bacillus coagulans* bacterium and about 85 pounds of sports nutrition composition. Optionally, the isolated *Bacillus coagulans* is in the form of a spore. Alternatively, the isolated *Bacillus coagulans* is in the form of a vegetative cell. In another aspect, the isolated *Bacillus coagulans* is in the form of a mixture of vegetative cells and spores. Preferably, the isolated *Bacillus coagulans* is in the form of a spore. More preferably, the bacterium is present as at least 80% spores, e.g., at least 85%, at least 90%, at least 95%, at least 98%, or at least 99% spores.

Bacterial species suitable for use in the methods describe herein include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or GANEDEN BC-30™, ATCC Designation Number PTA-6086; and GBI-40, ATCC Designation Number PTA-6087; see U.S. Pat. No. 6,849,256 to Farmer).

In some cases, the dry mix also includes a protein selected from the group consisting of soy protein, whey protein, rice protein, hemp seed protein, and casein protein. In other cases, the sports nutrition composition also includes creatine, calcium, sodium caseinate, whey peptides, and lactoferrin.

Methods of enhancing lean muscle development, recovery, or repair are carried out by administering to a subject desiring an enhancement of the lean muscle development, recovery or repair the compositions described herein, e.g., a composition comprising a sports nutrition composition and an isolated *Bacillus coagulans* spore, wherein the composition comprises at least 80% protein. The composition is optionally administered prior to or after an exercise period. For example, the composition is administered within 60 minutes of an exercise period, e.g., within 15 minutes, within 30 minutes, or within 45 minutes. Alternatively, the composition is administered within 2 hours, within 5 hours, or within 8 hours of an exercise period.

The absorption of the protein is increased in the subject after the administration of *Bacillus coagulans* in combination with protein as compared to the absorption of the protein after the administration of protein in the absence of *Bacillus coagulans*. For example, the rate of absorption ($t_{MAX}$) or overall absorption (from area under the curve $(AUC)_{0-4h}$ and $C_{MAX}$) are increased after the administration of *Bacillus coagulans* in combination with protein as compared to after the administration of protein in the absence of *Bacillus coagulans*, as measured by changes in amino acid levels in, e.g., blood over a one hour test period, a two hour test period, a four hour test period, an eight hour test period, a twelve hour test period, or a twenty-four hour test period. For example, protein absorption is increased by at least 10%, 50%, 2-fold, 5-fold, 10-fold, or more following administration of protein and *Bacillus coagulans* compared to protein without *Bacillus coagulans*.

The absorption of a vitamin is increased in the subject after the administration of *Bacillus coagulans* in combination with protein as compared to the absorption of the vitamin after the administration of protein in the absence of *Bacillus coagulans*. Exemplary vitamins include vitamin A, vitamin $B_1$, vitamin $B_2$, vitamin $B_3$, vitamin $B_5$, vitamin $B_6$, vitamin $B_7$, vitamin $B_9$, vitamin $B_{12}$, or vitamin C, vitamin D, vitamin E, and vitamin $K_1$.

In other cases, the absorption of a chemical element is increased in the subject after the administration of *Bacillus coagulans* in combination with protein as compared to the absorption of the chemical element after the administration of protein in the absence of *Bacillus coagulans*. Exemplary chemical elements include sodium, potassium, calcium, iron, and zinc.

Optionally, the *Bacillus coagulans* aids in the digestion of the sports nutrition composition, e.g., protein. For example, abdominal bloating, intestinal pain, passage of gas, loose bowel movements, and excessive abdominal gurgling are reduced following consumption of protein and *Bacillus coagulans* compared to the consumption of protein without *Bacillus coagulans*. However, subjects ingesting the product preferably have not been diagnosed with gastrointestinal disease or an inflammatory bowel condition.

The compositions are also useful in the prophylactic or therapeutic treatment of conditions associated with gastrointestinal infection by various pathogens, thereby supporting digestive health. The probiotic sports nutrition compositions of the invention are also used in the methods described herein for boosting the immune system. In some cases, the combination of *Bacillus coagulans* and protein works synergistically resulting in an enhanced inhibition of pathogens in the gastrointestinal tract of a subject, as compared to the administration of either *Bacillus coagulans* or protein alone. In other cases, the combination of *Bacillus coagulans* and protein works synergistically resulting in an enhanced boost of the immune system, as compared to the administration of either *Bacillus coagulans* or protein alone.

Optionally, the compositions of the invention additionally comprise L-alanine and/or inosine to promote the germination of the spores in the stomach and/or small intestine.

A probiotic lactic acid-producing bacteria suitable for use in the methods and compositions of the invention produces acid and is non-pathogenic. Purified and/or isolated *Bacillus coagulans* is particularly useful as a probiotic in the compositions described herein. By "purified" or "substantially purified" is meant a *Bacillus coagulans* bacterium that is substantially free of contaminating microorganisms or other macromolecules, e.g., polysaccharides, nucleic acids, or proteins.

Purified defines a degree of sterility that is safe for administration to a human subject, e.g., lacking infectious or toxic agents. Specifically, as used herein, an "isolated" or "purified" *Bacillus coagulans* or protein is substantially free of other cellular material, culture medium, chemical precursors, or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

The *Bacillus coagulans* Hammer strains of the invention are non-pathogenic and generally regarded as safe for use in human nutrition (i.e., GRAS classification) by the U.S. Federal Drug Administration (FDA) and the U.S. Department of Agriculture (USDA), and by those skilled in the art. Furthermore, the *Bacillus coagulans* Hammer strains of the invention germinate at or below human body temperature, rendering them useful as probiotics. Many *Bacillus coagulans* strains outside the Hammer group have mostly industrial applications, little or no nutritional benefit, and environmental contaminants that have not been evaluated for safety. Moreover, many other non-Hammer strains of *Bacillus coagulans* grow optimally at temperatures that exceed human body temperature and, thus, do not germinate efficiently in the human body. Such strains are less or not suitable as probiotics for human consumption.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

DETAILED DESCRIPTION OF THE INVENTION

The probiotic organisms of the invention are non-pathogenic, non-toxigenic, retain viability during storage, and survive passage through the stomach and small intestine. Non-pathogenic lactic acid-producing bacteria (i.e., "lactic acid bacteria"), such as the exemplary *Bacillus coagulans*, remain viable and retain their beneficial probiotic properties in sports nutrition compositions. Prior to the invention described herein, probiotics were very susceptible to harsh environment of the stomach and small intestine. Unlike other probiotics that die in the stomach or small intestine, the probiotic organisms described herein, e.g., *Bacillus coagulans* strain GBI-30 or GANEDEN BC-30™, ATCC Designation Number PTA-6086, germinate in the stomach and/or small intestine. Specifically, the probiotic spores described herein can survive passage through the stomach and small intestine.

Probiotic Lactic Acid-Producing Bacteria

The sports nutrition compositions include a lactic acid-producing bacterium, such as a spore-forming *Bacillus* species, e.g., *B. coagulans*. Preferably, the spore-forming *Bacillus* species of the invention is *B. coagulans* Hammer. There are many suitable bacteria identified as described herein, although the invention is not limited to currently known bacterial species insofar as the purposes and objectives of the bacteria is described. The property of acid production is important to the effectiveness of the probiotic lactic acid-producing bacteria of this invention.

Exemplary methods and compositions are described herein using *Bacillus coagulans* as a probiotic. Purified and/or isolated *Bacillus coagulans* is particularly useful as a probiotic in sports nutrition compositions. Probiotic *B. coagulans* is non-pathogenic and is generally regarded as safe (i.e., GRAS classification) by the U.S. Federal Drug Administration (FDA) and the U.S. Department of Agriculture (USDA), and by those skilled in the art.

*Bacillus coagulans* is a non-pathogenic gram positive spore-forming bacteria that produces L(+) lactic acid (dextrorotatory) in fermentation conditions. It has been isolated from natural sources, such as heat-treated soil samples inoculated into nutrient medium (Bergey's Manual off Systemic Bacteriology, Vol. 2, Sneath, P. H. A., et al., eds., Williams & Wilkins, Baltimore, Md., 1986). Purified *B. coagulans* strains have served as a source of enzymes including endonucleases (e.g., U.S. Pat. No. 5,200,336), amylase (U.S. Pat. No. 4,980,180), lactase (U.S. Pat. No. 4,323,651), and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes*; Sakaguti & Nakayama (ATCC 31284)) has been combined with other lactic acid producing bacteria and *B. natto* to produce a fermented food product from steamed soybeans (U.S. Pat. No. 4,110,477).

Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 (GANEDEN BC-30™), ATCC Designation Number PTA-6086; and GBI-40, ATCC Designation Number PTA-6087; see U.S. Pat. No. 6,849,256 to Farmer).

*Bacillus coagulans* was previously mis-characterized as a *Lactobacillus* and labeled as *Lactobacillus sporogenes*. However, initial classification was incorrect because *Bacillus coagulans* produces spores and excretes L(+)-lactic acid through metabolism. Both of these characteristics provide key features to the utility of *Bacillus coagulans*. These developmental and metabolic aspects required that the bacterium be classified as a lactic acid *Bacillus*. In addition, it is not generally appreciated that classic *Lactobacillus* species are unsuitable for colonization of the gut due to their instability in the harsh (i.e., acidic) pH environment of the bile, particularly human bile. By contrast, *Bacillus coagulans* ATCC Designation Number PTA-6085; GBI-30 (GANEDEN BC-30™) is able to survive and colonize the gastrointestinal tract in the bile environment and even grow in this low pH range.

Probiotic Activity of *Bacillus coagulans*

It is well-documented clinically that many species of bacterial, mycotic and yeast pathogens possess the ability to cause a variety of gastrointestinal disorders including, but not limited to disruption of normal gastrointestinal biochemical function, necrosis of gastrointestinal tissues, and disruption of the bioabsorption of nutrients, and like conditions. The probiotic microorganism-containing compositions described herein inhibit these pathogens. In the present case, subjects are generally healthy, e.g., they have not been diagnosed with a gastrointestinal disease (e.g., irritable bowel syndrome or Crohn's disease), an inflammatory bowel condition, or an autoimmune disease. The compositions and methods described herein are useful to increase absorption of protein and/or macro nutrients in a nutritional composition.

In one aspect, a *Bacillus coagulans* strain is included in the composition in the form of vegetative cells. In another aspect, the *Bacillus coagulans* strain is included in the composition in the form of spores. The invention also provides for including the *Bacillus coagulans* strain in the composition in the form of a powder, a dried cell mass, a stabilized paste, or a stabilized gel.

Because *Bacillus* spores are heat and pressure-resistant and can be stored as a dry powder, they are particularly useful for formulation into and manufacture of products such as the various sports nutrition compositions described herein. Specifically, the probiotic organisms described herein, e.g., *Bacillus coagulans* strain GBI-30 or GANEDEN BC-30™, ATCC Designation Number PTA-6086, survive passage through the stomach and small intestine. A *Bacillus* species is well suited for the present invention, particularly species having the ability to form spores which are relatively resistant to heat and other conditions, making them ideal for storage (shelf-life) in product formulations, e.g., sports nutrition compositions. Due to the shelf-stable properties of the *Bacillus coagulans* strains described herein, e.g., *Bacillus coagulans* strain GBI-30 or GANEDEN BC-30™, ATCC Designation Number PTA-6086, the product formulations of the invention are not confined to a refrigerator and may be stored at room temperature. The *Bacillus coagulans* of the invention survives storage (shelf-life) from about 12 days to about 2 years; from about 1 month to about 18 months; from about 3 months to about 1 year; or from about 6 months to about 9 months.

The probiotic organisms described herein, e.g., *Bacillus coagulans* strain GBI-30 or GANEDEN BC-30™, ATCC Designation Number PTA-6086, promote digestive and oral health and support the immune system. The ability of *Bacillus coagulans* to inhibit various bacterial pathogens was quantitatively ascertained by use of an in vitro assay. This assay is part of a standardized bacterial pathogen screen (developed by the U.S. Food and Drug Administration (FDA)) and is commercially available on solid support disks (DIFCO® BACTROL® Antibiotic Disks). To perform the assay, potato-dextrose plates (DIFCO®) were initially prepared using standard procedures. The plates were then individually inoculated with the bacteria (approximately $1.5 \times 10^6$ CFU) to be tested so as to form a confluent bacterial bed.

Inhibition of microorganisms (e.g. gastrointestinal pathogens) by *Bacillus coagulans* was subsequently ascertained by placing approximately $1.8 \times 10^6$ CFU of *Bacillus coagulans* in 10 µl of broth or buffer, directly in the center of the potato-dextrose plate with one test locus being approximately 8 mm in diameter per plate. A minimum of three test loci were used for each assay. The negative control consisted of a 10 µl volume of a sterile saline solution, whereas the positive control consisted of a 1 µl volume of glutaraldehyde. The plates were then incubated for approximately about 18 hr at 30° C., at which time the zones of inhibition were measured. As designated herein, "excellent inhibition" means the zone was 10 mm or greater in diameter; and "good inhibition" means the zone was greater than 2 mm in diameter but less than 10 mm in diameter.

As expected, no "inhibition" was seen with the negative, saline control, and excellent "inhibition" (approximately 16.2 mm diameter; average of three tests) was seen with the positive, glutaraldehyde control. For the enteric microorganisms tested, the following inhibition by *Bacillus coagulans* was found: (i) *Clostridium* species—excellent inhibition; (ii) *Escherichia coli*—excellent inhibition; (iii) *Clostridium* species—excellent inhibition, where the zone of inhibition was consistently greater than 15 mm in diameter. Similarly, excellent inhibition was also seen for the opportunistic pathogens *Pseudornonas aeruginosa*, and *Staphylococcus aureus*. Pathogenic enteric bacteria which were inhibited by *Bacillus coagulans* activity include, but are not limited to: *Staphylococcus aureus*; *Staphylococcus epidermidis*; *Streptococcus pyogenes*; *Pseudomonas aeruginosa*; *Escherichia coli* (enterohemorragic species); numerous *Clostridium* species (e.g., *Clostridium perfingens, Clostridium botulinum, Clostridium tributrycum, Clostridium sporogenes*, and the like); *Gardnereia vaginails; Proponbacterium aenes; Aeromonas hydrophia; Aspergillus* species; *Proteus* species; and *Klebsiella* species.

Micro-Encapsulation

In one aspect, the lactic-acid producing bacteria are incorporated into a microcapsule coating prior to addition to the sports nutrition composition, using any micro-encapsulation process well-known in the art. The isolated *Bacillus coagulans* are packaged, or encapsulated, within another material in order to protect the bacteria from the surrounding environment. The capsules of the invention range in size from one-thousandth of a millimeter to seven millimeters. The internal ingredients of the microcapsule are released from their shells in various ways, including mechanical rupture of the capsule wall, dissolution of the wall, melting of the wall and diffusion through the wall. Thus, micro-encapsulation provides additional protection to the isolated *Bacillus* bacterium during manufacturing and storage of the sports nutrition compositions of the invention. Physical methods of micro-encapsulation include pan coating, air-suspension coating, centrifugal extrusion, vibrational nozzle, and spray-drying. Chemical methods of micro-encapsulation include interfacial polymerization, in-situ polymerization, and matrix polymerization.

Alternatively, the lactic-acid producing bacteria is added to the sports nutrition composition without micro-encapsulation.

Probiotic Sports Nutrition Compositions

The invention includes a method of increasing protein absorption, enhancing lean muscle development, and/or increasing lean body mass by administering to a subject a composition comprising a *Bacillus coagulans* spore in a composition comprising at least 50% purified or processed protein, e.g., a composition that contains at least 75% whey protein or other protein source. The sports nutrition compositions are suitable for human or animal consumption. A typical subject is a healthy adult, e.g., greater than 16 years old. Alternatively, the sports nutrition compositions may also be administered to children under 18 years of age, e.g., under 15 years of age, under 10 years of age, or under 5 years of age. Alternatively, the sports nutrition compositions are administered to children and adults of all ages. The subject is a human being that desires to increase muscle development, strength or lean body mass, or an animal, e.g., livestock or performance animal such as a work animal or a race horse, for which an increase in muscle development or strength is desired. The compositions are also useful to confer clinical benefit to individuals that are suffering from or at risk of developing a muscle wasting condition, e.g., cachexia, as a result of disease such as cancer or infection.

Sports nutrition compositions are prepared by mixing dry powder ingredients (e.g., protein and *Bacillus coagulans*). Sports nutrition compositions include bodybuilding or body maintenance foods, e.g., weight gainers, commonly used by those involved in bodybuilding and athletics. They include protein (the most widely used such sports nutrition composition), amino acids, glutamine, essential fatty acids, meal replacement products, prohormones, creatine, thermogenic products, testosterone boosters, and branched-chain amino acids (BCAA). The three branched-chain amino acids (BCAAs) include leucine, isoleucine, and valine. Unlike other amino acids, BCAAs are metabolized in the muscle and have an anabolic/anti-catabolic effects. BCAAs account for 33% of muscle protein. Amino acids are the building blocks of protein, which the body metabolizes in the stomach and intestines. Protein powder contains amino acids such as isoleucine, alanine, leucine, arginine, lysine, aspartate, aspartic acid, methionine, cysteine, phenylalanine, threonine, tryptophan, glycine, valine, proline, histidine, serine, tyrosine, asparagine, selenocysteine, pyrrolysine, glutamate, glutamic acid, and glutamine.

Glutamine is the most abundant amino acid found in human muscle; however, the body's natural glutamine stores are depleted during anaerobic exercise. Thus, the sports nutrition compositions of the invention optionally include glutamine. Serum glutamine is used by the body to counteract acidosis resulting from exercise. In order to replenish the loss of glutamine from the bloodstream, the body catabolizes glutamine from the muscle. Thus, ingestion of glutamine combats muscle tissue wasting.

Suitable types of protein include soy protein, whey protein, rice protein, hemp protein, casein protein, and egg-white protein (e.g., egg albumin). Soy protein isolated from soybeans contains isoflavones, a type of phytoestrogen. Whey protein contains high levels of all the essential amino acids and branched-chain amino acids. For example, the amino acids regarded as essential for humans are phenylalanine, valine, threonine, tryptophan, isoleucine, methionine, leucine, lysine, and histidine. Whey protein also has the highest content of the amino acid cysteine, which aids in the biosynthesis of glutathione. For this reason, whey protein provides amino acids to aid in muscle recovery. Whey protein is derived from the process of making cheese from milk. There are two types of whey protein: whey concentrate (29%-89% protein by weight) and whey isolate (90%+ protein by weight). Another type of protein includes rice protein, which is made from whole grain, a complete protein source that is highly digestible and allergen free. Hemp protein from hemp seed contains complete and highly-digestible protein. Hemp oil is high in essential fatty acids, i.e., alpha-linolenic acid (an omega-3 fatty acid) and linoleic acid (an omega-6 fatty acid). Casein protein (or milk protein) has glutamine, and casomorphin. Finally, egg-white protein is a lactose- and dairy-free protein.

Proteins come in various forms, including protein powder, ready to drink protein shakes, bars, bites, oats, and gels. Protein powders are available in a wide variety of flavors including pineapple, orange, fruit punch, mixed berry, mango, cookies and cream, strawberry, strawberry banana, French vanilla, vanilla, vanilla ice cream, vanilla milkshake, banana, banana cream, Dutch chocolate, mocha cappuccino, double rich chocolate, chocolate caramel, chocolate milkshake, extreme milk chocolate, chocolate mint, chocolate chip, and chocolate. The protein powder is mixed with water, milk or juice (e.g., grapefruit juice, grape juice, orange juice, etc.), and often flavoring, resulting in a form known as a "protein shake" (as in milkshake) or "pudding". Protein powder is generally consumed immediately before or after exercising, or in place of a meal. The theory behind this regimen is that having a sufficient protein intake allows for efficient growth and repair of muscle tissue. Protein powders also aid in fat loss, muscle building, and slow the aging process.

Meal replacement products (MRPs) are either pre-packaged powdered drink mixes or edible bars designed to replace prepared meals. MRPs are generally high in protein, low in fat, have a low to moderate amount of carbohydrates, and contain a wide array of vitamins and minerals. The majority of MRPs use whey protein, casein (often listed as calcium caseinate or micellar casein), soy protein, and/or egg albumin as protein sources. Carbohydrates are typically derived from maltodextrin, oat fiber, brown rice, and/or wheat flour. Some MRPs also contain flax seed oil powder as a source of essential fatty acids.

Sports nutrition compositions may also contain other additional ingredients that are beneficial for bodybuilding, including calcium, sodium caseinate, whey peptide, glutamine peptides, L-glutamine, calcium alpha-ketoglutarate, additional amino acids, lactoferrin, conjugated linoleic acid, medium chain triglycerides, and creatine (e.g., creatine monohydrate). Creatine is a nitrogenous organic acid that is found in the muscle tissue of vertebrates mainly in the form of phosphocreatine replenishment of ATP, and supplies energy for muscle contraction. Creatine improves strength, energy, muscle mass, recovery times, brain function, and reduces mental fatigue. Creatine is available in a variety of forms, including creatine monohydrate and creatine ethyl ester.

Although it is known that athletes and bodybuilders may need an increased intake of protein, the exact amount is highly individualized and dependent on the type and duration of the exercise as well as the physiological make up of the individual. Research by Tarnopolsky et al. (1988) showed that for bodybuilding individuals, 1.97 g of protein per kg of body weight per day is recommended, whereas endurance athletes require 1.37 g/kg/d of protein. Studies suggest that there are different protein requirements for anaerobic and aerobic exercise. Endurance athletes in aerobic activity may have increased daily protein intake at 1.2-1.4 g per kg body weight per day, whereas strength training athletes performing anaerobic activity may have increased daily protein intake needs at 1.4-1.8 g per kg body weight so as to enhance muscle protein synthesis or to make up for the loss of amino acid oxidation during exercise.

Preferably, the sports nutrition composition ingredients are blended together as dry ingredients. Exemplary ingredients of the sports nutrition compositions described herein include protein and *Bacillus coagulans*. An exemplary strain of *Bacillus coagulans* suitable in the sports nutrition compositions described herein includes GBI-30 or GANEDEN BC-30™, ATCC Designation Number PTA-6086.

The dry mix for sports nutrition compositions comprises an isolated *Bacillus coagulans* bacterium. The dry mix is approximately 1 billion CFU of *Bacillus coagulans* bacterium per unit dose. Optionally, the dry mix is about 15% *Bacillus coagulans* bacterium and 85% protein. For example, about 100 pounds of dry mix contains about 15 pounds of *Bacillus coagulans* bacterium and about 85 pounds of protein. The dry mix is between about 1% and about 50% by weight of the sports nutrition composition, e.g., about 1% to about 20%, about 5% to about 15%; about 6%, about 7%, about 8%, about 9%, or about 10% by weight of the sports nutrition composition. For example, a 3 gram sports nutrition composition contains about 7% dry mix by weight of the sports nutrition composition. A 3.8 to 4 gram sports nutrition composition contains about 8-9% dry mix by weight of the sports nutrition composition.

As the recommended dietary allowances (RDA or recommended daily intake; RDI) is about $1 \times 10^9$ bacterium (according to EU guidelines), preferably, the sports nutrition composition comprises at least about $1 \times 10^9$ viable bacteria. In another aspect, the sports nutrition composition comprises at least about $1 \times 10^6$ to $1 \times 10^7$; at least about $1 \times 10^7$ to $1 \times 10^8$; or at least about $1 \times 10^8$ to $1 \times 10^9$ viable bacteria.

The *Bacillus* and/or *Bacillus coagulans* in the form of a dried spore composition is mixed with dry whey powder or is applied using any of a variety of known methods including, for example, applying a powder, spray-drying the probiotic onto the sports nutrition composition, or soaking the composition in a solution containing the probiotic. Any of a variety of methods for placing the bacterial composition into a sports nutrition composition can be used. In one aspect, a "spray-dry" method is used, in which the compositions are exposed in a low humidity chamber to an atomized mix containing a liquid composition, where the chamber is subsequently exposed to approximately 80-110° F. to dry the liquid, thereby impregnating the material of the sports nutrition composition with the components.

In some cases, *Bacillus coagulans* bacteria in the form of a spray-dried powder is included in or on the surface of the sports nutrition compositions described herein. Preferably, the isolated *Bacillus coagulans* is in the form of a spore, as the *Bacillus coagulans* spores of the invention are protected by a hardened coating that can withstand gastric acid and bile salts for delivery to the small and large intestines. The isolated *Bacillus coagulans* are at least 85%, at least 90%, at least 95%, or at least 99% pure spores. Alternatively, the isolated *Bacillus coagulans* is in the form of a vegetative cell. In one aspect, the isolated *Bacillus coagulans* are at least 85%, at least 90%, or at least 95% pure vegetative cells. In another aspect, the isolated *Bacillus coagulans* is in the form of a mixture of vegetative cells and spores. The *Bacillus coagulans* mixture is 90% spores, 10% vegetative cells; 75% spores, 25% vegetative cells; 60% spores, 40% vegetative cells; 50% spores, 50% vegetative cells; 60% vegetative cells, 40% spores; 75% vegetative cells, 25% spores; or 90% vegetative cells, 10% spores.

In one aspect, the amount of bacteria is about $10^4$ to $10^{14}$ colony forming units (CFU) of bacteria per gram of probiotic composition (i.e., vegetative cells and/or bacterial spores), preferably $10^5$ to $10^{13}$ CFU/g of sports nutrition composition. Alternatively, the concentrations are $10^8$ to $10^{13}$ CFU/g; $10^9$ to $10^{12}$ CFU/g; or $10^{10}$ to $10^{11}$ CFU/g of sports nutrition composition. In one aspect, the amount of bacteria is about $1\times10^6$ CFU per gram of sports nutrition composition. The actual amount in a sports nutrition composition will vary. A typical concentration is from approximately $1\times10^7$ to $1\times10^{12}$ CFU; $1\times10^8$ to $1\times10^{11}$ CFU; or $1\times10^9$ to $1\times10^{10}$ CFU of viable bacterium or spores/g of sports nutrition composition.

Following drying, the sports nutrition composition is ready for immediate use or for storage in a sterile package, e.g., a 3-ounce package (e.g., a bag or a bottle), a 6-ounce package, a 9-ounce package, a 12-ounce package, a 15-ounce package, an 18-ounce package, a 24-ounce package, a 48-ounce package, 80-ounce package, or 100-ounce package. In another example, the dried powder is packaged in unit dose quantities, e.g., 5 grams, 10 grams, 20 grams, 30 grams, 40 grams, 50 grams, 60 grams, 70 grams, 80 grams, 90 grams, or 100 gram packets. Alternatively, the dried powder is packaged in bulk, e.g., about 500 grams, about 600 grams, about 700 grams, about 800 grams, about 900 grams, about 1,000 grams, about 1,250 grams, about 1,500 grams, about 1,750 grams, about 2,000 grams, about 2,250 grams, about 2,500 gram, or about 3,000 gram containers. In one aspect, the invention provides for storing the sports nutrition composition in a sterile package at room temperature prior to consumption. Alternatively, the composition is consumed immediately.

The active ingredients (i.e., *Bacillus coagulans* and protein), comprise between about 0.01% to about 10%; 0.01% to about 1%; or about 0.05% to about 0.1% by weight of the probiotic sports nutrition composition. Optionally, the isolated *Bacillus coagulans* comprise about 1 mg to about 10 g; about 10 mg to about 1 g; or about 25 mg to about 75 mg by weight of the probiotic composition. Most preferably, the amount of *Bacillus coagulans* bacteria is about $5\times10^7$ colony forming units (CFU) of bacteria per gram of food matrix.

In some cases, the *Bacillus coagulans* spores are incorporated into any type of dry or lyophilized product which is dissolved or mixed with water, milk, or juice, so long as the temperature of the *Bacillus coagulans* spore-containing mixture is raised to the required heat-shock temperature (i.e., 80° C. for 5 minutes) necessary for germination of the spores. The *Bacillus coagulans* spores may either be incorporated into the dry or lyophilized product by the manufacturer of the product or by the consumer during preparation.

The *Bacillus coagulans* spores survive storage (shelf-life), i.e., retain viability or the ability to germinate at physiological conditions (e.g., ingestion), from about 12 days to about 2 years; from about 1 month to about 18 months; from about 3 months to about 1 year; or from about 6 months to about 9 months.

Example 1: Preparation of *Bacillus coagulans* Cultures

*Bacillus coagulans* Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg $MnSO_4$, and 1,000 ml distilled water, adjusted to pH 7.0, using a standard airlift fermentation vessel at 30° C. The range of $MnSO_4$ acceptable for sporulation is 1 mg/l to 1 g/l. The vegetative cells can actively reproduce up to 45° C., and the spores are stable up to 90° C. After fermentation, the *B. coagulans* bacterial cells or spores are collected using standard methods (e.g., filtration, centrifugation) and the collected cells and spores can be lyophilized, spray-dried, air-dried or frozen.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing *B. coagulans* Hammer spores at room temperature is about 10 years.

Example 2: Preparation of *Bacillus coagulans* Spores

A culture of dried *B. coagulans* spores was prepared as follows. Ten million spores were inoculated into a one liter culture containing 24 g potato dextrose broth, 10 g of enzymic-digest of poultry and fish tissue, 5 g of FOS and 10 g $MnSO_4$. The culture was maintained for 72 hours under a high oxygen environment at 37° C. to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP). A dried composition that comprises at least about 75% (e.g., 80%, 85%, or 90%) spores is then mixed with protein powder.

Example 3: *Bacillus coagulans* Spores Survive in the Gastric Environment

This study was performed in order to determine the survivability rate of *Bacillus coagulans* spores as they pass through the stomach. Samples of *Bacillus coagulans* spores were subjected to a simulated gastric environment for varying lengths of time in order to attain their survivability rate. First, a homogeneous sample of raw material *Bacillus coagulans* of at least 12 grams was prepared. Saline solution at pH 1 was prepared using 3N HCl (150 mls each into six 250 ml media bottles) and sterilized. Additional saline solutions with pH 2 and 3 were prepared similarly, resulting in 6 sterile 250 ml bottles, each containing 150 ml pH adjusted saline. Six sterile 250 ml media bottles each containing 150 ml normal saline solution were prepared and sterilized. Phosphate buffer (~400 ml) was prepared at pH 7.2. Test tubes (24) were prepared and sterilized, each containing 9 ml of phosphate buffer pH 7.2. Test tubes (120) were prepared, each containing 9 ml of normal saline. GYE (glucose-yeast extract) agar medium was prepared and sterilized and cooled to 45° C. in a water bath. Samples (24) of raw material were weighed, each ~500 milligrams (theoretically equivalent to 10 billion spores). The samples were added to media bottles at 37° C. and incubated half for 20 minutes the other half for 120 minutes. After 20 and 120 minutes incubation, respectively, the samples were mixed to uniformity and pipet 1 ml into 9 ml of sterile phosphate buffer pH 7.2. After all 12 samples from each time point were placed into test tubes containing sterile phosphate buffer, serial dilutions were made until 6 tubes had been used for each sample. The final dilution for the final two test tubes were $3 \times 10^7$ and $3 \times 10^8$, which gave a count of roughly 300 and 30 CFU, respectively. The final 2 test tubes from each sample were placed into 70° C. water bath for 30 minutes. After 30 minutes, they were cooled immediately to 45° C. Three sterile petri plates per tube were set out. 1.0 ml from the heat-treated tube was added into each petri plate, then 15 ml of sterile molten GYE Agar medium (at 45° C.) was poured into each of the petri plates and mixed thoroughly. When solidified, the plates were incubated in an inverted position for 48 hours at 40° C. The individual colonies were counted. Results were expressed as CFU per gram as shown in Table 1 below. $1.0E+10=1\times10^{10}$.

TABLE 1

| Sample | 20 Minutes Incubation Spore Count, CFU/gram | 120 Minutes Incubation Spore Count, CFU/gram |
| --- | --- | --- |
| Normal Saline - A | 1.90E+10 | 1.88E+10 |
| Normal Saline - B | 2.12E+10 | 2.00E+10 |
| Normal Saline - C | 1.64E+10 | 2.06E+10 |
| Average | 1.89E+10 | 1.98E+10 |
| Saline pH 1.0 - D | 2.08E+09 | 5.98E+07 |
| Saline pH 1.0 - E | 1.47E+09 | 0.00E+00 |
| Saline pH 1.0 - F | 3.59E+09 | 0.00E+00 |
| Average | 2.38E+09 | 1.99E+07 |
| Saline pH 2.0 - G | 3.63E+09 | 3.46E+09 |
| Saline pH 2.0 - H | 4.47E+09 | 2.48E+09 |
| Saline pH 2.0 - I | 3.58E+09 | 2.82E+09 |
| Average | 3.89E+09 | 2.92E+09 |
| Saline pH 3.0 - J | 1.65E+10 | 1.13E+10 |
| Saline pH 3.0 - K | 1.35E+10 | 1.11E+10 |
| Saline pH 3.0 - L | 1.80E+10 | 1.39E+10 |
| Average | 1.60E+10 | 1.21E+10 |

Example 4: The Effects of a Probiotic on the Absorption of Protein and Micronutrients in Healthy Males The effects of the probiotic GANEDEN BC-30™ (Bacillus coagulans ATCC Designation Number PTA-6086) on protein and micronutrient absorption is evaluated in healthy males following a 14-day period. The protocol outlined below determines the effect of a probiotic product (GANEDEN BC-30™, Bacillus coagulans ATCC Designation Number PTA-6086) in combination with protein as compared to protein in the absence of Bacillus coagulans on protein absorption, both rate of absorption ($t_{Max}$) and overall absorption (from area under the curve ($AUC_{0-4h}$) and $C_{Max}$), as measured by changes in blood amino acid levels over a four hour test period. The protocol outlined below is also designed to determine the effect of a probiotic product (GANEDEN BC-30™, Bacillus coagulans ATCC Designation Number PTA-6086) in combination with protein as compared to protein in the absence of Bacillus coagulans on vitamin and mineral absorption, both rate of absorption ($t_{Max}$) and overall absorption (from $AUC_{0-4h}$ and $C_{Max}$), as measured by changes in blood levels of select vitamins (vitamins B6, B12 and C) and minerals (calcium, iron and zinc) over a four hour test period. The study also determines the effect of a probiotic product (GANEDEN BC-30™, Bacillus coagulans ATCC Designation Number PTA-6086) in combination with protein as compared to protein in the absence of Bacillus coagulans on gastrointestinal (GI)-specific symptoms using a GI questionnaire after 14 days of treatment.

The period of evaluation lasts approximately four weeks with subjects attending a screening/randomization visit and two follow-up test visits. Eligible subjects take GANEDEN BC-30™ (Bacillus coagulans ATCC Designation Number PTA-6086) plus protein and protein alone, each for 14 days, in random order. After each 14-day period, there is a test visit at which subjects take the test product (probiotic plus protein or protein alone) and a multiple vitamin and mineral supplement. Blood is collected at baseline (prior to the test product) and at 1, 2, 3 and 4 hours following product administration. Levels of various amino acids, vitamins and minerals are measured so that the effects of the probiotic on protein and micronutrient absorption are determined. The probiotic increases the absorption of the protein and micronutrients by increasing the efficiency of the gut by balancing the intestinal flora or by increasing the acidity of the stomach for more efficient breakdown of the nutrients.

Although the study population is comprised of generally healthy adults that do not have GI disorders or symptoms, there may be beneficial effects in GI health with the administration of GANEDEN BC-30™ (Bacillus coagulans ATCC Designation Number PTA-6086). A six item questionnaire is used to assess changes in GI health (e.g. abdominal pain, bloating and gas) with lower incidence indicating positive effects with regard to GI health.

Study Design

The study described herein is a prospective, randomized, double blind, placebo controlled, crossover clinical trial. A total of 10 male subjects are enrolled, with each subject receiving the two test products, in a randomly-assigned sequence. Each subject serves as his own control.

Study Population:

The study population includes 10 male subjects, aged 21 to 60 years, that do not have any gastrointestinal disease or inflammatory bowel condition, and who are not taking on a regular basis any prescription or over-the counter medications for any gastrointestinal problems.

Test Products:

Product 1—GANEDEN BC-30™ (Bacillus coagulans strain GBI-30, ATCC Designation Number PTA-6086) plus Protein.

Product 2—Protein (placebo; no probiotic).

Duration of Study

Excluding the screening visit, each subject completing the study participates for approximately four weeks, ±three days.

Efficacy Assessments:

Efficacy variables consist of protein absorption [rate of absorption ($t_M$) and overall absorption ($AUC_{0-4h}$ and $C_{Max}$) of blood amino acids], vitamin absorption [rate of absorption ($t_{Max}$) and overall absorption ($AUC_{0-4h}$ and $C_{Max}$) of vitamins B6, B12 and C], mineral absorption [rate of absorption ($W_{Max}$) and overall absorption ($AUC_{0-4h}$ and $C_{Max}$) of minerals calcium, iron and zinc], and GI questionnaire scores (abdominal pain, abdominal bloating, gas, bowel movements, gurgling noises and overall well-being).

Efficacy endpoints generally consist of changes in efficacy variables from baseline to four hours post product administration following 14 days of product use. These changes (endpoints) are then be compared between the two products.

Statistical Methods:

For each efficacy endpoint (amino acid, vitamin, and mineral blood concentration), the following non-compartmental pharmacokinetic (PK) parameters are calculated:

$C_{Max}$ The maximum concentration observed during the four post-dose samples;

$t_{max}$ the time at which the maximum concentration was observed;

$AUC_{0-4h}$ the area under the concentration-vs-time curve above the baseline (time 0) concentration, integrated from time 0 to 4 hours post-dose, by trapezoidal-rule quadrature.

All safety and efficacy variables are summarized by time point and by product. Numerical variables are presented as mean, standard deviation, count, median, and range (minimum to maximum value). Changes from the appropriate baseline are summarized and presented in the same way. Numerical variables and their changes from baseline are displayed graphically, as plots of mean value vs. time, with separate lines for the two products (probiotic vs. placebo). Categorical variables are presented as tabulations of counts and percentages of totals.

For each continuous variable, the mean change from baseline to each subsequent time point are tested for nominal significance by the paired Student t test, or by the non-parametric Wilcoxon test if non-normally distributed. The mean differences in the variable, or in the change in that variable from baseline, between the different products are tested for nominal significance by the paired Student t test or by the non-parametric Wilcoxon test if non-normally distributed. For each categorical variable, difference in the distribution of categories between the different product groups are tested for nominal significance by the Fisher Exact test if possible, or by the Chi-Square test if necessary.

Adverse events (AEs) are listed, Medical Dictionary for Regulatory Activities (MedDRA) encoded, grouped by general type of event (gastrointestinal, neurologic, cardiac, etc.), and cross-tabulated by event type and product. Differences in AE patterns between the two products are tested by the Fisher Exact test. Subjective remarks are categorized to the extent possible, and analyzed for pattern differences between the two products in the same way as AE's.

The pharmacokinetic endpoints ($C_{Max}$, $t_{Max}$, and $AUC_{0-4h}$) after 14 days of product use are tested for significance between the two products by a repeated-measures analysis of variance (RM-ANOVA) for each endpoint, where the value of the variable at each point in time is the repeated dependent variable, and the product identification (GANEDEN BC-30™, Bacillus coagulans ATCC Designation Number PTA-6086+Protein or Placebo) is the main factor. If the efficacy variables are not normally distributed, and cannot be normalized by logarithmic or other transformations, then between-product testing are carried out using the Wilcoxon signed-ranks test.

Assuming 15% attrition during the course of the study, there are about 8 or 9 analyzable subjects remaining in the per-protocol population. To have 80% power to obtain significance ($p \leq 0.05$) when testing a change over time (over 14 days of product use) within a product group, the mean change is about equal to about 15% larger than the standard deviation of the changes (a "1.15-sigma" effect size). To show that there was a significant difference between the two products, the mean difference is about 65% larger than the within-group variability of the endpoint (a "1.65-sigma" effect size).

Each efficacy endpoint is considered an independent question of interest, and is tested independently at the 0.05 alpha level ($p \leq 0.05$ required for a conclusion of statistical significance). Multiple testing is taken into account when the results of the efficacy analyses are interpreted by the statistician in the Final Statistical Report.

Study Population

Inclusion Criteria
1. Male subjects, aged 21 to 60 years
2. Subject is able to understand and sign the informed consent to participate in the study.
3. Subject is willing and able to comply with the protocol including:
   a. Attending three visits;
   b. Refraining from eating any yogurt or lacto-fermented beverages during the study;
   c. Refraining from using any dietary supplements or nutritionals during the study;
   d. Not taking any new vitamin and/or mineral supplements until after study completion and refraining from taking any vitamin and/or minerals supplements for 24 hours prior to the test visits.

Exclusion Criteria
1. Subject has any of the following medical conditions:
   a. active heart disease
   b. uncontrolled high blood pressure ($\geq$ 140/90 mmHg)
   c. renal or hepatic impairment/disease
   d. Type I or II diabetes
   e. bipolar disorder
   f. Parkinson's disease
   g. unstable thyroid disease
   h. immune disorder (such as human immune deficiency virus (HIV)/acquired immune deficiency syndrome (AIDS))
   i. psychiatric disorders (hospitalized within the past one year)
   j. any medical condition deemed exclusionary by the Principal Investigator (PI)
2. Subject has a history of cancer (except localized skin cancer without metastases) within five years prior to screening.
3. Subject has a history of or currently has any gastrointestinal disease or disorder or any inflammatory bowel condition such as Crohn's disease, short bowel, ulcerative colitis, or Irritable Bowel Syndrome (IBS).
4. Subject is lactose intolerant (self-professed or diagnosed).
5. Subject has had any stomach or intestinal surgery (i.e. gastric bypass).
6. Subject takes on a regular basis (defined as two or more times per week) any prescription or over-the counter medications for diarrhea, constipation, heartburn or any other gastrointestinal problems.
7. Subject is currently taking laxatives or has taken laxatives within the 30 days prior to screening/enrollment.
8. Subject is currently taking antibiotics (or any drug that significantly interferes with bacterial flora) or has taken antibiotics within the 60 days prior to screening/enrollment.

9. Subject is currently taking or has used in the past 30 days probiotics/prebiotics (including yogurt and lacto-fermented beverages) or any digestive enzymes [prescription or over-the-counter (OTC)]. Thirty-day washout allowed.
10. Subject is on an unstable dose of medication (defined as fewer than 90 days at the same dose).
    a. Anti-hypertensives and anti-hyperlipidemic medications ok if stable dose.
11. Subject is currently taking any medication deemed exclusionary by PI.
12. Subject has an allergy to soy, milk, chocolate or any of the ingredients in the test product.
13. Subject has a history of drug or alcohol abuse in the past 12 months.
14. Subject has begun/stopped smoking ≤6 months ago OR has plans to begin/quit smoking.
15. Subject has any condition or abnormality that, in the opinion of the investigator, would compromise the safety of the subject or the quality of the study data.
16. Subject is participating or has participated in another research study within 30 days prior to the screening visit.

Concomitant Medications and Other Substances
Substances Permitted During the Study
Subjects may take the following substances during their participation in this study:
  Vitamins and/or minerals subject was taking prior to starting the study (same frequency as prior to study start). However, subjects cannot take any vitamins and/or minerals for the 24 hours prior to the test visits. If the subject was not previously taking vitamins and/or minerals, he is asked to not start taking any during the study.
  Thyroid hormone replacement therapy, if drug and dose are unchanged for at least 90 days before screening and throughout the study.
  Antihypertensive and antihyperlipidemic medications, if drug and dose are unchanged for at least 90 days before screening and throughout the study.

Substances not Permitted During the Study
  Subjects may not take the following substances for at least 60 days prior to the screening/randomization visit (visit 1) or throughout the study. Any subject taking these substances during the study is evaluated by the PI.
    All oral antibiotics including: Amoxil®, Trimox® (amoxicillin), Cipro® (ciprofloxacin), Flagyl® (metronidazole), Doxy-100® (doxycyline) and Bactrim® Double Strength (trimethoprim-sulfamethoxazole).
    Any medications that significantly interfere with bacterial flora
  Subjects may not take the following substances for at least 30 days prior to the screening/randomization visit (visit 1) or throughout the study. Any subject taking these substances during the study is evaluated by the PI.
    Laxatives: psyllium husk (Metamucil), methylcellulose (Citrucel), polycarbophil, docusate (Colace, Diocto), mineral oil, sodium phosphate (and variants), magnesium citrate, magnesium hydroxide (Milk of magnesia), magnesium sulfate (which is Epsom salt), glycerin suppositories, sorbitol, lactulose, and polyethylene glycol (PEG)
    Digestive enzymes: Cotazym, Creon, Pancrease, Digex, Dygase, Gastrinex, Hi-Vegi-Lip, Ku-Zyme, Kutrase, Lactaid, Lapase, Lipram, Palcaps 10, Pan-2400, Pancreatin, Pancrecarb, Pangestyme, Panocaps, Panokase, Sucraid, SureLac, Ultrase, Viokase, Zenpep
    All dietary and herbal supplements including:
      Probiotic products (including fortified foods): *Acidophilus*, Bacid, Flora-Q, Florastor, Novaflor, RisaQuad, Superdophilus, GANEDEN BC-30™ (*Bacillus coagulans* ATCC Designation Number PTA-6086), LAFTI B94, LAFTI L10, LAFTI L26, Bifiene, Align, Howaru Bifido, ProBactrix, Mutaflor, Actimel/DanActive, Cultura, Yakult, *Lactobacillus fortis*, GoodBelly/ProViva/TuZen, LGG, Vifit, *Verum*, DiarSafe, Bion Flore Intime, Jarrow, Fem-Dophilus, Florajen3, Bio-K, CL1285, A'Biotica;
      Prebiotic products (including fortified foods): lactulose, lactitol oligofructose, inulin, galacto-oligosaccharides, tagatose, isomaltooligosaccharides, polydextrose, maltodextrin, fructo-oligosaccharides, arabinogalactan, polyols-lactulose;
      Those supplements purported to improve GI health including dandelion, devil's claw, feverfew, ginger, goldenseal, lemon balm, peppermint, roman chamomile, turmeric, valerian, yarrow, mastic gum, dill, caraway, anise, cumin.

Diet
  Subjects are required to fast (no food or beverage other than water, no caffeine) for eight hours prior to visits 2 and 3. Subjects are asked to refrain from alcohol for the 24 hours prior to visits 2 and 3. Subjects are not allowed to eat yogurt or to drink lacto-fermented beverages throughout the study period. Examples of lacto-fermented beverages include kefir (water and dairy), kambucha, kvass, cider and ginger ale.
  Subjects are not allowed to use protein powders (e.g. whey, soy, hemp, pea, rice) while participating in the study.
  Subjects are not allowed to eat/drink foods and beverages high in vitamin C for 24 hours prior to the test visits. Examples of foods and beverages high in vitamin C include citrus fruits (such as oranges and grapefruit) and their juices, red and green pepper, kiwifruit, broccoli, strawberries, cantaloupe, baked potatoes, and tomatoes.
  Other than this, subjects are allowed to continue their normal diet.

Exercise
  Subjects are asked to refrain from exercise for the 24 hours prior to visits 2 and 3.
Subjects are allowed to continue their usual exercise routine.

Product Ingredients
  The following lists of ingredients are provided.
Product 1: GANEDEN BC-30™ (*Bacillus coagulans* ATCC Designation Number PTA-6086)+Protein
  1 billion CFU GANEDEN BC-30™ (*Bacillus coagulans* ATCC Designation Number PTA-6086) and 23 g of whey protein (whey protein isolate (WPI)>90) in 30 g of powder, chocolate flavor.
Product 2: Protein (placebo)
  23 g of whey protein (WPI>90) in 30 g of powder, chocolate flavor.
Nutrition Facts for the Whey Protein Powder

| Serving Size: 1 Packet | |
|---|---|
| Amount Per Serving | |
| Calories 130 Calories from fat 25 | |
| | % Daily Value* |
| Total Fat 2.5 g | 4% |
| Saturated Fat 1 g | 5% |
| Trans Fat 0 g | |

| | |
|---|---|
| Cholesterol 65 mg | 22% |
| Sodium 50 mg | 2% |
| Potassium 170 mg | 5% |
| Total Carbohydrate 3 g | 1% |
| Dietary Fiber 1 g | 4% |
| Sugars 1 g | |
| Protein 23 g | 46% |
| Vitamin A | 0% |
| Vitamin C | 0% |
| Calcium | 10% |
| Iron | <2% |

*Percent Daily Values are based on a 2,000 calorie diet.

Ingredients: Whey Protein Concentrate (Whey Protein Concentrate, Soy Lecithin), Whey Protein Isolate, Cocoa Powder (Processed with Alkali), Natural & Artificial Flavors, Acesulfame Potassium and Sucralose.

At the test visits, subjects are provided a multiple vitamin with mineral supplement. The supplement that is used is the One A Day® Men's Health Formula.

The ingredients in the One A Day Men's Health Formula

Calcium Carbonate, Magnesium Oxide, Microcrystalline Cellulose, Ascorbic Acid, Croscarmellose Sodium, Gelatin, Maltodextrin; Less than 2% of: Beta-Carotene, Biotin, Cholecalciferol, Chromium Chloride, Crospovidone, Cupric Oxide, Cyanocobalamin, D-Calcium Pantothenate, dl-Alpha-Tocopheryl Acetate, Folic Acid, Hydroxypropyl Methylcellulose, Lycopene, Manganese Sulfate, Niacinamide, Phytonadione, Polyethylene Glycol, Pyridoxine Hydrochloride, Riboflavin, Silicon Dioxide, Sodium Selenate, Soybean Oil, Starch, Stearic Acid, Thiamine Mononitrate, Triacetin, Vitamin A Acetate and Zinc Oxide.

Product Dosing

Product administration instructions: Subjects are instructed to take one packet per day, at approximately the same time of day.

Preparation instructions: Mix one packet with six to eight ounces of cold water, milk or subject's preferred beverage for 20 to 30 seconds in a shaker or blender.

Subjects are instructed to start taking the first study product the day after visit 1. Subjects are instructed to not take the study product prior to coming in for visits 2 and 3 (i.e. not take study product the morning of visits 2 and 3). Subjects are required to take the study product on site for visits 2 and 3. Subjects are instructed to start the second study product the day after visit 2. Subjects cannot take anything the evening of visit 2. Subjects are instructed to bring the remaining product to all visits.

Product Administration Instructions

Take one packet per day, at approximately the same time of day; mix with 6 to 8 ounces of water, milk or favorite beverage and shake/blend for 20 to 30 seconds.

The product is packaged so that the subject is provided only the quantity needed for the time between visits (14 days) plus product to cover the window (additional three days of product).

Product Compliance

Compliance is measured via the packet counting method. By documenting the number of calendar days between visits and the number of packets that should have been taken, compliance is calculated. The subject's compliance is recorded (as a % of prescribed amount) for each product and this compliance % is used to establish the subject's eligibility for inclusion in the populations (Safety, Intent-to-Treat, and/or Per-Protocol) used for analysis of the study's results, in accordance with the criteria specified below.

For visits 2 and 3, product administration are performed on site. Documentation is done in each subject's source confirming product administration.

Randomization

The consulting statistician develops a randomization schedule and create a randomization log for use at the investigative site. To minimize the effect of treatment sequence (carry-over, training, fatigue, seasonality, etc.) on safety and efficacy endpoints, the active product (A) and placebo (B) are administered to each subject in one of the two possible sequences: A-B or B-A. Block-2 randomization is used, so that the two possible product sequences are shuffled into random order for assignment for the first two subjects, then shuffled again into a different random permutation for assignment to the next two subjects, and so on for the remaining subjects to be enrolled (plus additional spare product).

Study Procedures

Informed Consent

An informed consent form (ICF) is written in accordance with established criteria of the Institutional Review Board (IRB) and the appropriate federal regulations (e.g., 21 CFR Parts 50 and 56) to describe the study plan, procedures, and risks. The investigator and the IRB must all approve the ICF and any ICF amendments or administrative changes before they are used.

Investigators ensure that each subject is clearly and fully informed of the purpose, potential risks, and requirements of study participation. Written informed consent must be obtained from each subject before performing any screening or other study procedures.

Medical History

A Medical History is performed at the screening visit to collect information on past and current medical conditions, surgical history, allergy information, and concomitant or recently taken (in the past 90 days) medications including over the counter (OTC) non-prescription products, nutritional supplements, herbals, and investigational products.

Physical Examination

Subjects undergo a full physical examination at screening for determining eligibility.

Vital Signs

At each visit, subjects have blood pressure and heart rate measured.

The following guidelines are used for the blood pressure and heart rate: subjects sit in a chair, resting, for at least five minutes prior to taking the measurements. Measurements are done with subjects in a seated position and the subject's left arm is used.

Study Questionnaires

Dichotomous Questionnaire—the following is administered at visits 2 and 3. Each subject is asked:
Did you:
Not eat or drink any foods or beverages other than water or have caffeine for the eight hours prior to the visit?
Eat or drink any foods or beverages high in vitamin C in the past 24 hours?
Drink any alcoholic beverages in the past 24 hours?
Take any vitamin and/or mineral supplements in the past 24 hours?
Exercise in the past 24 hours?
Use any new vitamin and/or mineral supplements since the screening visit?
Use any protein powder other than the study product since the screening visit?

Use any dietary supplements, any probiotics, or prebiotics since 30 days prior to the screening visit?

Eat or drink any yogurt or lacto-fermented beverages since 30 days prior to the screening visit?

Did you take the study product today?

If subject answers "yes" to any of the above questions, the subject is discontinued as per PI discretion and/or a protocol deviation is recorded.

GI Questionnaire—a six-part questionnaire regarding general well-being and gastrointestinal symptoms is administered at visits 1, 2 and 3. Subjects are asked, "how often in the past two weeks have you" experienced various GI symptoms with answer choices of "all of the time, most of the time, sometimes, a little and never". Subjects are asked to rate how they feel overall with answer choices of "better, same and worse". See, e.g., Worthley et al., 2009 Am J Clin Nutr, 90: 578-586. For example, the following questions are asked:

1) How often in the past week have you had pain in the abdomen?
2) How often in the past week have you experienced abdominal bloating?
3) How often in the past week have you been troubled by excessive passage of gas through the anus?
4) How often in the past week have you been troubled by frequent of loose bowel movements?
5) How often in the past week have you been troubled by excessive gurgling noises from the abdomen?
6) In comparison to how you felt at the start of the study, over the past week, have you felt better, worse or the same?

Protein and Micronutrient Absorption Test

The following test is performed at visits 2 and 3 to assess the effects of the products on protein, vitamin and mineral absorption.

The following is performed to standardize the testing conditions:

The test is performed after an eight hour fast;
Subjects are not physically active during the test;
No smoking is allowed during the test.

Test Procedure:

Collect the baseline blood sample (0 hours) for the evaluation of the baseline levels of various amino acids and select vitamins and minerals.

Provide subject with the multiple vitamin with mineral supplement (can be taken with water or the study product).

Provide subject with the study product which is to be consumed within 10 minutes.

Timing of the test is from when the subject begins to drink the study product.

Collect blood samples at 1, 2, 3, and 4 hours for the evaluation of the absorption of the amino acids, vitamins and minerals.

During the Time between Blood Draws:

Subjects are primarily sitting.
Subjects are allowed to walk around the site to use the rest room and to stretch but are not allowed to do any additional physical activity.
Subjects are allowed to do restful activities such as read, listen to music with earphones, watch television, work on the computer or rest/sleep.
Subjects are not allowed to eat or drink anything other than water.

Descriptive Summarization

For each efficacy endpoint (amino acid, vitamin, and mineral blood concentration), the following non-compartmental pharmacokinetic (PK) parameters is calculated:

$C_{Max}$ The maximum concentration observed during the four post-dose samples;

$t_{Max}$ the time at which the maximum concentration was observed; $AUC_{0-4h}$ the area under the concentration-vs-time curve above the baseline (time 0) concentration, integrated from time 0 to 4 hours post-dose, by trapezoidal-rule quadrature.

All safety and efficacy variables are summarized by time point and by product. Numerical variables are presented as mean, standard deviation, count, median, and range (minimum to maximum value). Changes from the appropriate baseline are summarized and presented in the same way. Numerical variables and their changes from baseline are displayed graphically, as plots of mean value vs. time, with separate lines for the two products (probiotic vs. placebo). The graphs may contain vertical error-bars around the mean values, indicated standard errors of the mean, if, in the opinion of the statistician, this would make the graphs more informative. Categorical variables are presented as tabulations of counts and percentages of totals.

For each continuous variable, the mean change from baseline to each subsequent time point are tested for nominal significance by the paired Student t test, or by the non-parametric Wilcoxon test if non-normally distributed.

For each continuous variable at each time point, the mean differences in the variable, or in the change in that variable from baseline, between the different products are tested for nominal significance by the paired Student t test or by the non-parametric Wilcoxon test if non-normally distributed.

For each categorical variable, difference in the distribution of categories between the different product groups are tested for nominal significance by the Fisher Exact test if possible, or by the Chi-Square test if necessary.

All p-values appearing in these summarizations is considered descriptive, not inferential. No final statistical conclusions are drawn from them, but they are referred to in the interpretation of the changes.

Statistical Analysis

Safety and Efficacy Variables and Endpoints

Safety variables consist of adverse events and subjective remarks.

Safety endpoints consist of the changes in the safety variables listed above with each product following 14 days of treatment.

There is no formal safety objective.

Efficacy variables consist of protein absorption [rate of absorption ($t_{Max}$) and overall absorption ($AUC_{0-4h}$ and $C_{Max}$) of blood amino acids], vitamin absorption [rate of absorption ($t_{Max}$) and overall absorption ($AUC_{0-4h}$ and $C_{Max}$) of vitamins B6, B12 and C], mineral absorption [rate of absorption ($t_{Max}$) and overall absorption ($AUC_{0-4h}$ and $C_{Max}$) of minerals calcium, iron and zinc], and GI questionnaire scores (abdominal pain, abdominal bloating, gas, bowel movements, gurgling noises and overall well-being).

Efficacy endpoints generally consist of changes in efficacy variables from baseline to four hours post product administration following 14 days of product use. These changes (endpoints) are then compared between the two products.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of enhancing lean muscle development, recovery, or repair, comprising administering to a subject desiring an enhancement of said lean muscle development, recovery, or repair, a composition comprising: (a) a protein powder, said powder isolated protein absorbable by said subject, said isolated protein consisting of one or more of isolated egg albumin protein, isolated soy protein, isolated pea protein, isolated hemp protein, or isolated rice protein; and (b) an isolated *Bacillus coagulans*, wherein
the *Bacillus coagulans* is *Bacillus coagulans* strain GBI-30 (ATCC Designation Number PTA-6086),
the *Bacillus coagulans* is present as at least 75% spores;
said composition comprises at least 50% protein by weight; and
said composition contains about 20 grams to about 50 grams of said isolated protein per serving.

2. The method of claim 1, wherein said composition comprises at least 75% protein by weight.

3. The method of claim 1, wherein the amount of said isolated protein absorbed by said subject is at least 50% greater as compared to the amount of said isolated protein absorbed after administration in the absence of *Bacillus coagulans*.

4. The method of claim 1, further comprising administering to said subject a vitamin absorbable by said subject, wherein the amount of said vitamin absorbed by said subject is increased as compared to the amount of said vitamin absorbed after administration in the absence of *Bacillus coagulans*.

5. The method of claim 4, wherein said vitamin comprises vitamin A, vitamin Bi, vitamin $B_2$, vitamin $B_3$, vitamin $B_5$ vitamin $B_6$, vitamin $B_7$, vitamin $B_9$, vitamin $B_{12}$, or vitamin C, vitamin D, vitamin E, or vitamin $K_1$.

6. The method of claim 1, further comprising administering to said subject a chemical element absorbable by said subject, wherein the amount of said chemical element absorbed by said subject is increased as compared to the amount of said chemical element absorbed after administration in the absence of *Bacillus coagulans*.

7. The method of claim 6, wherein said chemical element comprises sodium, potassium, calcium, iron, or zinc.

8. The method of claim 1, further comprising administering a vitamin or mineral.

9. The method of claim 1, wherein the composition is administered within 8 hours of an exercise period.

10. The method of claim 1, wherein the subject suffers from a muscle wasting condition.

11. The method of claim 1, wherein the protein powder and the *Bacillus coagulans* are blended together as dry ingredients.

12. The method of claim 1, wherein the composition comprises about 85% protein by weight.

13. The method of claim 1, wherein the *Bacillus coagulans* is present in the form of a spray-dried powder in the composition.

14. The method of claim 1, wherein the *Bacillus coagulans* is present as at least 90% spores.

15. The method of claim 1, wherein the *Bacillus coagulans* is present in an amount of about 1 billion colony forming units (CPU) per serving.

16. The method of claim 2, wherein said composition comprises at least 90% protein by weight.

17. The method of claim 1, further comprising administering whey protein to said subject.

18. The method of claim 1, wherein said protein powder contains isolated soy protein.

19. The method of claim 1, wherein said protein powder contains isolated pea protein.

20. The method of claim 1, wherein said protein powder contains isolated egg albumin protein.

21. The method of claim 1, wherein said protein powder contains isolated hemp protein.

22. The method of claim 1, wherein said protein powder contains isolated rice protein.

23. The method of claim 1, wherein said *Bacillus coagulans* spores have retained the ability to germinate in said composition for from about 6 months to about 9 months.

24. The method of claim 1, wherein said *Bacillus coagulans* spores have retained the ability to germinate in said composition for from about 1 month to about 18 months.

25. The method of claim 1, wherein said *Bacillus coagulans* spores have retained the ability to germinate storage in said composition for from about 3 months to about 1 year.

26. The method of claim 1, wherein the strength of said subject is increased compared to a subject administered said isolated protein in the absence of *Bacillus coagulans*.

27. A method of increasing absorption of micronutrients and protein in a subject who has not been diagnosed with a gastrointestinal disease, an inflammatory bowel condition, or an autoimmune disease, comprising administering to said subject a composition comprising: (a) a protein powder, said powder isolated protein absorbable by said subject, said isolated protein consisting of one or more of isolated egg albumin protein, isolated soy protein, isolated pea protein, isolated hemp protein, or isolated rice protein; (b) a vitamin absorbable by said subject; (c) a chemical element absorbable by said subject; and (d) an isolated *Bacillus coagulans*, wherein
the *Bacillus coagulans* is *Bacillus coagulans* strain GBI-30 (ATCC Designation Number PTA-6086),
the *Bacillus coagulans* is present as at least 75% spores;
said composition comprises at least 50% protein by weight; and
said composition contains about 20 grams to about 50 grams of said isolated protein per serving.

28. The method of claim 27, wherein said subject is an endurance athlete.

29. The method of claim 27, wherein said subject is a strength training athlete.

30. The method of claim 27, wherein the amount of said chemical element absorbed by said subject is increased as compared to the amount of said chemical element absorbed after administration of said chemical element in the absence of *Bacillus coagulans*, and wherein said chemical element comprises potassium.

31. The method of claim 1, wherein said composition comprises about 20 grams to about 50 grams of isolated egg albumin protein per serving.

32. The method of claim 1, wherein said composition comprises about 20 grams to about 50 grams of isolated soy protein per serving.

33. The method of claim 1, wherein said composition comprises about 20 grams to about 50 grams of isolated pea protein per serving.

34. The method of claim 1, wherein said composition comprises about 20 grams to about 50 grams of isolated hemp protein per serving.

35. The method of claim 1, wherein said composition comprises about 20 grams to about 50 grams of isolated rice protein per serving.

* * * * *